(12) United States Patent
Reiter et al.

(10) Patent No.: US 8,449,889 B2
(45) Date of Patent: May 28, 2013

(54) IMMUNO-MOLECULES CONTAINING VIRAL PROTEINS, COMPOSITIONS THEREOF AND METHODS OF USING

(75) Inventors: Yoram Reiter, Haifa (IL); Avital Lev, Dresher, PA (US)

(73) Assignee: Technion Research & Development Foundation Limited, Haifa (IL)

(*) Notice: Subject to any disclaimer, the term of this patent is extended or adjusted under 35 U.S.C. 154(b) by 0 days.

(21) Appl. No.: 13/235,625

(22) Filed: Sep. 19, 2011

(65) Prior Publication Data

US 2012/0003249 A1 Jan. 5, 2012

Related U.S. Application Data

(60) Division of application No. 10/482,532, filed as application No. PCT/IL02/00478 on Jun. 18, 2002, now Pat. No. 8,022,190, which is a continuation of application No. 10/108,511, filed on Mar. 29, 2002, now abandoned.

(60) Provisional application No. 60/298,915, filed on Jun. 19, 2001.

(51) Int. Cl.
*A61K 39/00* (2006.01)

(52) U.S. Cl.
USPC ..................................... 424/182.1

(58) Field of Classification Search
None
See application file for complete search history.

(56) References Cited

U.S. PATENT DOCUMENTS

| | | | |
|---|---|---|---|
| 5,194,425 A | 3/1993 | Sharma et al. | |
| 5,260,422 A | 11/1993 | Clark et al. | |
| 5,284,935 A | 2/1994 | Clark et al. | |
| 5,468,481 A | 11/1995 | Sharma et al. | |
| 5,635,363 A | 6/1997 | Altman et al. | |
| 5,820,866 A | 10/1998 | Kappler et al. | |
| 5,837,477 A | 11/1998 | Germain et al. | |
| 5,869,270 A | 2/1999 | Rhode et al. | |
| 5,976,551 A | 11/1999 | Mottez et al. | |
| 6,011,146 A | 1/2000 | Mottez et al. | |
| 6,015,884 A | 1/2000 | Schneck et al. | |
| 6,140,113 A | 10/2000 | Schneck et al. | |
| 6,153,408 A | 11/2000 | Abastado et al. | |
| 6,211,342 B1 | 4/2001 | Hirsch et al. | |
| 6,232,445 B1 | 5/2001 | Rhode et al. | |
| 6,248,564 B1 | 6/2001 | Walter et al. | |
| 6,548,067 B1 | 4/2003 | Seemann et al. | |
| 6,843,992 B2 | 1/2005 | Diamond | |
| 2003/0003535 A1 | 1/2003 | Reiter | |
| 2003/0016627 A1 | 1/2003 | MeLampy et al. | |
| 2003/0017134 A1 | 1/2003 | Reiter et al. | |
| 2004/0086960 A1 | 5/2004 | Reiter | |
| 2005/0063970 A1 | 3/2005 | Reiter et al. | |
| 2008/0014208 A1 | 1/2008 | Reiter et al. | |
| 2009/0148925 A1 | 6/2009 | Reiter | |
| 2009/0258393 A1 | 10/2009 | Reiter | |

FOREIGN PATENT DOCUMENTS

| | | |
|---|---|---|
| EP | 0352761 | 1/1990 |
| JP | 02-104599 | 4/1990 |
| JP | 2003-530836 | 10/2003 |
| WO | WO 87/06262 | 10/1987 |
| WO | WO 96/04314 | 2/1996 |
| WO | WO 97/24446 | 7/1997 |
| WO | WO 97/28191 | 8/1997 |
| WO | WO 99/14236 | 3/1999 |
| WO | WO 99/28471 | 6/1999 |
| WO | WO 99/64464 | 12/1999 |
| WO | WO 01/72768 | 10/2001 |
| WO | WO 01/78768 | 10/2001 |
| WO | WO 01/90198 | 11/2001 |
| WO | WO 02/36146 | 5/2002 |
| WO | WO 02/102299 | 12/2002 |
| WO | WO 02/102840 | 12/2002 |
| WO | WO 2007/136778 | 11/2007 |

OTHER PUBLICATIONS

Skolnick et al. (Trends in Biotechnology, 18: 34-39, 2000).*
Jones (Pharmacogenomics Journal, 1:126-134, 2001).*
Tosatto et al (Current Pharmaceutical Design, 12:2067-2086, 2006).*
Jain (Scientific American, 271(1):58-65, Jul. 1994).*
Dillman, (Annals of Internal Medicine, 111:592-603, 1989).*
Weiner (Seminars in Oncology, 26 (4 Suppl 12):41-50, Aug. 1999).*
Scher (JNCI, 92(23):1866-1868, 2000).*
Eccles (Int. J. Dev. Biol., 55:685-696, 2011).*
Office Action Dated Jan. 5, 2012 From the Patent Office of the State Intellectual Porperty Office of the People's Republic of China Re. Application No. 200780018196.5 and Its Translation Into English.
Examiner's Report Dated Jan. 18, 2012 From the Australian Government, IP Australia Re. Application No. 2007254167.
Examination Report Dated Mar. 19, 2012 From the Government of India, Patent Office, Intellectual Property Building Re. Application No. 2669/MUMNP/2008.
Office Action Dated Mar. 29, 2012 From the Israel Patent Office Re. Application No. 160412 and Its Translation Into English.
Fan et al. "Direct Binding of a Soluble Natural Killer Cell Inhibitory Receptor to a Soluble Human Leukocyte Antigen-Cw4 Class I Major Histocompatibility Complex Molecule", Proc. Natl. Acad. Sci. USA, 93(14): 7178-7183, Jul. 1996.
International Preliminary Examination Report Dated Sep. 3, 2004 From the International Preliminary Examining Authority Re.: Application No. PCT/IL02/00478.
Communication Pursuant to Article 94(3) EPC Dated Dec. 1, 2009 From the European Patent Office Re. Application No. 07777164.0.
Communication Pursuant to Article 94(3) EPC Dated Dec. 2, 2009 From the European Patent Office Re. Application No. 02733206.3.
Communication Pursuant to Article 94(3) EPC Dated Feb. 8, 2011 From the European Patent Office Re. Application No. 02733206.3.
Communication Pursuant to Article 94(3) EPC Dated Mar. 11, 2009 From the European Patent Office Re.: Application No. 01914159.7.
Communication Pursuant to Article 94(3) EPC Dated Mar. 24, 2011 From the European Patent Office Re. Application No. 07777164.0.
Communication Pursuant to Article 96(2) EPC Dated Aug. 6, 2007 From the European Patent Office Re. Application No. 02733206.3.
Communication Pursuant to Rules (70(2) and 70a(2) EPC and Reference to Rule 39(1) EPC Dated May 10, 2011 From the European Patent Office Re. Application No. 10166544.6.

(Continued)

Primary Examiner — Brad Duffy

(57) ABSTRACT

An immuno-molecule which comprises a soluble human MHC class I effector domain; and an antibody targeting domain which is linked to the soluble human MHC class I effector domain, methods of making same and uses thereof.

10 Claims, 8 Drawing Sheets

(5 of 8 Drawing Sheet(s) Filed in Color)

OTHER PUBLICATIONS

Communication Pursuant to Rules 161 and 162 EPC Dated Jan. 20, 2009 From the European Patent Office Re. Application No. 07777164.0.
European Search Report and the European Search Opinion Dated Mar. 16, 2011 From the European Patent Office Re. Application No. 10166544.6.
Examination Report Dated Jun. 9, 2008 From the Intellectual Property Office of New Zealand Re. Application No. 568650.
Examination Report Dated Dec. 14, 2009 From the Intellectual Property Office of New Zealand Re. Application No. 581793.
Examination Report Dated May 23, 2005 From the Intellectual Property Office of New Zealand Re. Applicaiton No. 530656.
Examination Report Dated Feb. 24, 2010 From the Intellectual Property Office of New Zealand Re. Application No. 581793.
Examination Report Dated Nov. 29, 2006 From the Intellectual Property Office of New Zealand Re. Applicaiton No. 530656.
Examination Report Dated Nov. 29, 2006 From the Intellectual Property Office of New Zealand Re. Application No. 551473.
Examiner's Report Dated Feb. 18, 2010 From the Australian Government, IP Australia Re.: Application No. 2007203607.
Examiner's Report Dated Feb. 19, 2007 From the Australian Government, IP Australia Re. Application No. 2002304279.
Examiner's Report Dated Aug. 27, 2010 From the Australian Government, IP Australia Re. Application No. 2008243241.
International Preliminary Examination Report Dated May 20, 2005 From the International Preliminary Examining Authority Re.: Application No. PCT/IL01/00260.
International Preliminary Report on Patentability Dated Dec. 4, 2008 From the International Bureau of WIPO Re. Application No. PCT/US2007/011953.
International Search Report Dated Dec. 12, 2007 From the International Searching Authority Re. Application No. PCT/US07/11953.
International Search Report Dated Oct. 17, 2002 From the International Searching Authority Re.: Application No. PCT/IL01/00260.
Interview Summary and Supplemental Response Dated Dec. 23, 2010 to Telephone Interview With Examiner on Dec. 21, 2010 in the US Patent and Trademark Office Re. U.S. Appl. No. 10/482,532.
Notice of Allowance Dated Feb. 14, 2011 From the US Patent and Trademark Office Re. U.S. Appl. No. 11/804,541.
Notice of Allowance Dated May 16, 2011 From the US Patent and Trademark Office Re. U.S. Appl. No. 10/482,532.
Notice of Allowance Dated May 31, 2011 From the Canadian Intellectual Property Office Re. Application No. 2,451,353.
Notification Dated Jul. 1, 2010 From the Polish Patent Office Re. Application No. P-373302 and Its Translation Into English.
Office Action Dated Sep. 7, 2010 From the Israel Patent Office Re. Application No. 160412 and Its Translation Into English.
Office Action Dated Dec. 16, 2010 From the Israel Patent Office Re. Application No. 195191.
Office Action Dated Feb. 19, 2009 From the Israeli Patent Office Re.: Application No. 151860 and Its Translation Into English.
Office Action Dated May 21, 2008 From the Israeli Patent Office Re.: Application No. 151860.
Office Action Dated Apr. 26, 2007 From the Israeli Patent Office Re.: Application No. 151860.
Office Action Dated Jan. 27, 2011 From the Patent Office of the State Intellectual Porperty Office of the People's Republic of China Re. Application No. 200780018196.5 and Its Translation Into English.
Official Action Dated Jan. 4, 2011 From the US Patent and Trademark Office Re. U.S. Appl. No. 10/482,532.
Official Action Dated Apr. 5, 2007 From the US Patent and Trademark Office Re.: U.S. Appl. No. 10/073,300.
Official Action Dated May 5, 2010 From the US Patent and Trademark Office Re. U.S. Appl. No. 10/482,532.
Official Action Dated Oct. 6, 2006 From the US Patent and Trademark Office Re.: U.S. Appl. No. 10/073,300.
Official Action Dated Apr. 8, 2005 From the US Patent and Trademark Office Re.: U.S. Appl. No. 10/073,300.
Official Action Dated Oct. 8, 2010 From the US Patent and Trademark Office Re. U.S. Appl. No. 10/508,531.
Official Action Dated Apr. 10, 2006 From the US Patent and Trademark Office Re.: U.S. Appl. No. 10/075,257.
Official Action Dated Jan. 11, 2007 From the US Patent and Trademark Office Re.: U.S. Appl. No. 10/075,257.
Official Action Dated Oct. 11, 2010 from the Eurasian Patent Office Re. Application No. 200870555/28 and Its Translation into English.
Official Action Dated Mar. 16, 2006 From the United States Patent and Trademark Office Re.: U.S. Appl. No. 10/073,300.
Official Action Dated Apr. 17, 2008 From the US Patent and Trademark Office Re. U.S. Appl. No. 10/482,532.
Official Action Dated May 17, 2010 From the US Patent and Trademark Office Re. U.S. Appl. No. 11/804,541.
Official Action Dated Dec. 18, 2008 From the US Patent and Trademark Office Re.: U.S. Appl. No. 10/075,257.
Official Action Dated Dec. 18, 2009 From the US Patent and Trademark Office Re. U.S. Appl. No. 11/804,541.
Official Action Dated Mar. 18, 2008 From the United States Patent and Trademark Office Re.: U.S. Appl. No. 10/075,257.
Official Action Dated Mar. 18, 2011 From the US Patent and Trademark Office Re.: U.S. Appl. No. 12/486,794.
Official Action Dated Sep. 19, 2007 From the US Patent and Trademark Office Re.: U.S. Appl. No. 10/073,300.
Official Action Dated Mar. 20, 2007 From the US Patent and Trademark Office Re. U.S. Appl. No. 10/482,532.
Official Action Dated Aug. 22, 2011 From the Uktainian Ministry of Education and Science, State Department of Intellectual Property Re. Application No. a 2008 14602 and Its Translation Into English.
Official Action Dated Jul. 23, 2009 From the US Patent and Trademark Office Re. U.S. Appl. No. 10/482,532.
Official Action Dated Oct. 24, 2005 From the US Patent and Trademark Office Re.: U.S. Appl. No. 10/075,257.
Official Action Dated Feb. 25, 2005 From the US Patent and Trademark Office Re.: U.S. Appl. No. 10/075,257.
Official Action Dated Aug. 26, 2004 From the United States Patent and Trademark Office Re.: U.S. Appl. No. 10/073,300.
Official Action Dated Dec. 27, 2010 From the US Patent and Trademark Office Re. U.S. Appl. No. 10/482,532.
Official Action Dated Jul. 27, 2007 From the Its Patent and Trademark Office Re. U.S. Appl. No. 10/482,532.
Official Action Dated Jul. 28, 2004 From the United States Patent and Trademark Office Re.: U.S. Appl. No. 10/075,257.
Official Action Dated Apr. 29, 2010 From the US Patent and Trademark Office Re.: U.S. Appl. No. 12/486,794.
Official Action Dated Aug. 30, 2007 From the US Patent and Trademark Office Re.: U.S. Appl. No. 10/075,257.
Official Action Dated Sep. 30, 2009 From the US Patent and Trademark Office Re. U.S. Appl. No. 11/804,541.
Official Action Dated Sep. 30, 2010 From the United States Patent and Trademark Office Re.: U.S. Appl. No. 12/213,368.
Requisition by the Examiner Dated Jun. 7, 2011 From the Canadian Intellectual Property Office Re.: Application No. 2,404,489.
Requisition by the Examiner Dated Jan. 28, 2009 From the Canadian Intellectual Property Office Re.: Application No. 2,404,489.
Response Dated Jun. 1, 2010 to Official Action of Apr. 29, 2010 From the US Patent and Trademark Office Re.: U.S. Appl. No. 12/486,794.
Response Dated Jan. 2, 2011 to Notice of Reason for Rejection of Sep. 17, 2010 From the Japanese Patent Office Re. Application No. 2001-571699.
Response Dated Feb. 3, 2010 to Official Action Dated Dec. 18, 2009 and Supplemental Response to Official Action Dated Sep. 30, 2009 From the US Patent and Trademark Office Re. U.S. Appl. No. 11/804,541.
Response Dated Feb. 3, 2011 to Office Action of Sep. 7, 2010 From the Israel Patent Office Re. Application No. 160412.
Response Dated Apr. 4, 2011 to Official Action of Jan. 4. 2011 From the US Patent and Trademark Office Re. U.S. Appl. No. 10/482,532.
Response Dated May 4, 2011 to Official Action of Mar. 18, 2011 From the US Patent and Trademark Office Re.: U.S. Appl. No. 12/486,794.
Response Dated Nov. 4, 2010 to Official Action of May 5, 2010 From the US Patent and Trademark Office Re. U.S. Appl. No. 10/482,532.
Response Dated Feb. 12, 2010 to Examination Report of Dec. 14, 2009 From the Intellectual Property Office of New Zealand Re. Application No. 581793.

Response Dated Mar. 12, 2010 to Communication Pursuant to Article 94(3) EPC of Dec. 1, 2009 From the European Patent Office Re. Application No. 07777164.0.
Response Dated Apr. 13, 2010 to Communication Pursuant to Article 94(3) EPC of Dec. 2, 2009 From the European Patent Office Re. Application No. 02733206.3.
Response Dated Oct. 14, 2010 to Official Action of Sep. 30, 2009 From the US Patent and Trademark Office Re. U.S. Appl. No. 11/804,541.
Response Dated Nov. 17, 2010 to Official Action of May 17, 2010 From the US Patent and Trademark Office Re. U.S. Appl. No. 11/804,541.
Response Dated Apr. 20, 2007 to Official Action of Mar. 20, 2007 From the US Patent and Trademark Office Re. U.S. Appl. No. 10/482,532.
Response Dated Mar. 20, 2011 to Office Action of Jan. 27, 2011 From the Patent Office of the State Intellectual Porperty Office of the People's Republic of China Re. Application No. 200780018196.5.
Response Dated May 20, 2009 to Official Action of Apr. 17, 2008 From the US Patent and Trademark Office Re. U.S. Appl. No. 10/482,532.
Response Dated Jun. 21, 2010 to Examination Report of Feb. 24, 2010 From the Intellectual Property Office of New Zealand Re. Application No. 581793.
Response Dated Dec. 23, 2004 to Official Action of Aug. 26, 2004 From the US Patent and Trademark Office Re.: U.S. Appl. No. 10/073,300.
Response Dated Jan. 25, 2010 to Official Action of Jul. 23, 2009 From the US Patent and Trademark Office Re. U.S. Appl. No. 10/482,532.
Response Dated Nov. 25, 2004 to Official Action of Jul. 28, 2004 From the US Patent and Trademark Office Re.: U.S. Appl. No. 10/075,257.
Response Dated May 26, 2011 to Communication Pursuant to Article 94(3) EPC of Feb. 8, 2011 From the European Patent Office Re. Application No. 02733206.3.
Response Dated Jan. 28, 2008 to Official Action of Jul. 27, 2007 From the US Patent and Trademark Office Re. U.S. Appl. No. 10/482,532.
Response Dated May 28, 2008 to Examination Report of Nov. 29, 2006 From the Intellectual Property Office of New Zealand Re. Application No. 551473.
Supplemental Response Dated Jan. 31, 2011 to Official Action of May 17, 2010 From the US Patent and Trademark Office Re. U.S. Appl. No. 11/804,541.
Supplementary European Search Report Dated Aug. 24, 2004 From the European Patent Office Re.: Application No. EP 01914159.7.
Supplementary European Search Report and the European Search Opinion Dated Aug. 24, 2009 From the European Patent Office Re. Application No. 07777164.0.
Supplementary European Search Report Dated Apr. 3, 2007 From the European Patent Office Re. Application No. 02733206.3.
Translation of Decision of Rejection Dated Nov. 17, 2009 From the Japanese Patent Office Re. Application No. 2003-504888.
Translation of Final Notice of Rejection Dated Apr. 14, 2009 From the Japanese Patent Office Re. Application No. 2003-504888.
Translation of Notice of Reason for Rejection Dated Sep. 17, 2010 From the Japanese Patent Office Re. Application No. 2001-571699.
Translation of Notice of Reasons for Rejection Dated Aug. 5, 2008 From the Japanese Patent Office Re. Application No. 2003-504888.
Translation of Official Decision for Rejection Dated Apr. 15, 2011 From the Japanese Patent Office Re. Application No. 2001-571699.
Written Opinion Dated Oct. 4, 2004 From the International Preliminary Examining Authority Re.: Application No. PCT/IL01/00260.
Abastado et al. "Dimerization of Soluble Major Histocompatibility Complex-Peptide Complexes Is Sufficient for Activation of T Cell Hybridoma and Induction of Unresponsiveness", Journal of Experimental Medicine, p. 439-447, 1995. Abstract. p. 439, col. 2, p. 440, col. 1, § 1.
Altman et al. "Formation of Functional Peptide Complexes of Class II Major Histocompatibility Complex Proteins From Subunits Produced in *Escherichia coli*", Proc. Nat. Acad. Sci. USA 90: 10330-10334, 1993.

Berko et al. "Membrane-Anchored Beta2- Microglobulin Stabilizes a Highly Receptive State of MIIC Class I Molecules", The Journal of Immunology 174: 2116-2123, 2005.
Bird et al. "Single-Chain Antigen-Binding Proteins", Science, 242: 423-426, Oct. 21, 1988.
Bousso et al. "Enrichment of Antigen-Specific T Lymphocytes by Panning on Immobilized MHC-Peptide Complexes", Immunology Letters, 59(2): 85-91, 1997. Abstract p. 86, col. 1.
Brinkmann et al. "Independent Domain Folding of Pseudomonas Exotoxin and Single-Chain Immunotoxins: Influence of Interdomain Connections", Proc. Natl. Acad. Sci. USA 89: 3075-3079, Apr. 1992.
Burrows et al. "Two-Domain MHC Class II Molecules Form Stable Complexes With Myelin Basic Protein 69-89 Peptide That Detect and Inhibit Rat Encephalitogenic T Cells and Treat Experimental Autoimmune Encephalomyelitis", The Journal of Immunology, 161: 5987-5996, 1998.
Choc et al. "B3(Fab)-PE38M: A Recombinant Immunotoxin in Which a Mutant Form of Pseudomonas Exotoxin Is Fused to the Fab Fragment of Monoclonal Antibody B3", Cancer Research, 54: 3460-3467, Jul. 1, 1994.
Denkberg et al. "Recombinant Human Single-Chain MHC-Peptide Complexes Made From *E. coli* by In Vitro Refolding: Functional Single-Chain MHC-Peptide Complexes and Tetramers With Tumor Associated Antigens", European Journal of Immunology, XP002289070, 30(12): 3522-3532, 2000. Abstract. p. 3524, col. 1, § 2, From Bottom.
Garboczi et al. "HLA-A2-Peptide Complexes: Refolding and Crystallization of Molecules Expressed in *Escherichia coli* and Complexed With Single Antigenic Peptides", Proc. Natl. Acad. Sci. USA, XP002131069, 89: 3429-3433, 1992. Abstract. p. 3429, col. 1, § 1.
Godeau et al. "Organization of Phosphatidylcholine and Sphingomyelin in the Surface Monolayer of Low Density Lipoprotein and Lipoprotein(a) as Determined by Time-Resolved Fluorometry", The Journal of Biological Chemistry, 267(34): 24223-24229, Dec. 5, 1992.
Godeau et al. "Purification and Ligand Binding of a Soluble Class I Major Histocompatibility Complex Molecule Consisting of the First Three Domains of H-2Kd Fused to ?2-Microglobulin Expressed in the Baculovirus-Insect Cell System", The Journal of Biological Chemistry, 267(34): 24224-24229, Dec. 5, 1992.
Gr?goire et al. "Covalent Assembly of a Soluble T Cell Receptor-Peptide-Major Histocompatibility Class 1 Complex", Proc. Natl. Acad. Sci. USA, 93: 7184-7189, Jul. 1996.
Hassan et al. "Mesothelin: A New Target for Immunotherapy", Clinical Cancer Research, XP009076012, 10(12/Pt.01): 3937-3942, Jun. 15, 2004. p. 3940, 1-h Col., Last §—p. 3941, 1-h Col., § 2.
Hicklin et al. "HLA Class I Antigen Downregulation in Human Cancers: T-Cell Immunotherapy Revives an Old Story", Molecular Medicine Today, 5: 178-186, Apr. 1999.
Kourilsky et al. "Immunological Issues in Vaccine Trials: T-Cell Responses", Preclinical and Clinical Development of New Vaccines, 95: 117-124, 1998.
Lang et al. "High Frequency of Human Cytomegalovirus (IICMV)-Specific CD8 |T Cells Detected in a Healthy CMV-Seropositive Donor", Cellular and Molecular Life Sciences: CMLS, 59(6): 1076-1080, Jun. 2002. Abstract.
Lee et al. "A Recombinant Single-Chain HLA-A2.1 Molecule, With a Cis Active ?—2-Microglobulin Domain, Is Biologically Active in Peptide Binding and Antigen Presentation", Human Immunology, 49(1): 28-37, 1996.
Lee et al. "Functional Cell Surface Expression by a Recombinant Single-Chain Class I Major Histocompatibility Complex Molecule With a Cis-Active Beta 2-Microglobulin Domain", European Journal of Immunology, 24(11): 2633-2639, 1994.
Lev et al. "Tumor-Specific Ab-Mediated Targeting of MHC-Peptide Complexes Induces Regression of human Tumor Xenografts in Vivo", Proc. Natl. Acad. Sci. USA, PNAS, 101(24): 9051-9056, Jun. 15, 2004. Abstract, p. 9051, col. 1, § 1, col. 2, § 1, 2, 4, p. 9052, Fig.1B, col. 1, § 3, col. 2, § 3, p. 9055, col. 1, § 2, p. 9056, col. 2, § 2.
Lone et al. "In Vitro Induction of Specific Cytotoxic T Lymphocytes Using Recombinant Single-Chain MHC Class I/Peptide Complexes", Journal of Immunotherapy, 21(4): 283-94, 1998. & Third Keystone Symposium on Cellular Immunology and the Immunotherapy of Cancer.

Low et al. "Oral and Pulmonary Delivery of FSH-Fc Fusion Proteins Via Neonatal Fc Receptor-Mediated Transcytosis", Human Reproduction, 20(7): 1805-1813, 2005. p. 1806, col. 1, § 9.

Mabry III "Engineering Therapeutic Antibody Fragments Targeting the Anthrax Toxin", Dissertation, Presented to the Faculty of The Graduate School of the University of Texas at Austin for the Degree of Doctor of Philosophy, 182 P., Aug. 2005. p. 75, Fig.3.1.

Mage et al "A Recombinant, Soluble, Single-Chain Class 1 Major Histocompatibility Complex Molecule with Biological Activity", PNAS, 89: 10658-10662, 1992.

Mage et al. "A Recombinant, Soluble, Single-Chain Class 1 Major Histocompatibility Complex Molecule with Biological Activity", PNAS, 89: 10658-10662, 1992.

Matsumura et al. "In Vitro Peptide Binding to Soluble Empty Class I Major Histocompatibility Complex Molecules Isolated From Transfected Drososphila Mclanogaster Cells", Journal of Biological Chemistry, 267(33): 23589-23595, 1992.

Mottez et al. "Cells Expressing a Major Histocompatibility Complex Class I Molecule With a Single Covalently Bound Peptide Are Highly Immunogenic", Journal of Experimental Medicine, XP000654243, 181(2): 493-502, 1995. Abstract. p. 493, col. 2, p. 495, Fig. 1.

Ogg et al. "HLA-Peptide Tetrameric Complexes", Current Opinion in Immunology, 10: 393-396, 1998.

Ogg et al. "Sensitization of Tumour Cells to Lysis by Virus-Specific CTL Using Antibody-Targeted MHC Class I/Peptide Complexes", British Journal of Cancer, 82(5): 1058-1062, 2000.

Ojcius et al. "Dissociation of the Peptide-MHC Class I Complex Limits the Binding Rate of Exogenous Peptide", Journal of Immunology, 151(11): 6020-6026, 1993.

Oved et al. "Antibody-Mediated Targeting of Human Single-Chain Class I MHC With Covalently Linked Peptides Induces Efficient Killing of Tumor Cells by Tumor or Viral-Specific Cytotoxic T Lymphocytes", Cancer Immunology and Immunotherapy, XP019333169, 54(9): 867-879, Sep. 1, 2005.

Parker et al. "Peptide Binding to HLA-A2 and HLA-B27 Isolated From *Eschericia coli*", The Journal of Biological Chemistry, 267(8): 5451-5459, 1992.

Parker et al. "Sequence Motifs Important for Peptide Binding to the Human MHC Class I Molecule, HLA-A2", Journal of Immunology, 149(11): 3580-3587, 1992.

Patamawenu et al. "Generation of Functional HLA-A2 Molecules Covalently Attached to Antigenic Peptides", Thesis (Master of Science in Biomedical Science), University of Maryland, 1988. Abstract.

Rammensee et al. "MHC Molecules as Peptide Receptors", Current Opinion Immunology, 5(1): 35-44, 1993.

Reti?re et al. "Generation of Cytomegalovirus-Specific Human T-Lymphocyte Clones by Using Autologous B-Lymphoblastoid Cells With Stable Expression of PP65 or IE1 Proteins: A Tool to Study the Fine Specificity of the Antiviral Response", Journal of Virology, 74(9): 3948-3952, May 2000.

Riddell et al. "Class I MHC-Restricted Cytotoxic T Lymphocyte Recognition of Cells Infected With Human Cytomegalovirus Does Not Require Endogenous Viral Gene Expression", The Journal of Immunology, 146(8): 2795-2804, Apr. 15, 1991. Abstract.

Robert et al. "Antibody-Conjugated MHC Class I Tetramers Can Target Tumor Cells for Specific Lysis by T Lymphocytes", European Journal of Immunology, XP001021944, 30(11): 3165-3170, Nov. 2000. Abstract, p. 3168, r-h Col.

Rotzschke et al. "Isolation and Analysis of Naturally Processed Viral Peptides as Recognized by Cytotoxic T Cells", Nature, 384: 252-254, 1990.

Shields et al. "Characterization of the Interactions Between MHC Class I Subunits: A Systematic Approach for the Engineering of Higher Affinity Variants of Beta2-Microglobulin", The Journal of Imunology,160: 2297-2307, 1998.

Sylvester-Hvid et al. "A Single-Chain Fusion Molecule Consisting of Peptide, Major Histocompatibility Gene Complex Class I Heavy Chain and ?2-Microglobulin Can Fold Partially Correctly, But Binds Peptide Inefficiently", Scandinavian Journal of Immunology, XP002240676, 50(4): 355-352, 1999. p. 357, col. 1, § 1, p. 358, col. 1, Fig.2, p. 358, col. 2, ff.

Tafuro et al. "Reconstitution of Antigen Presentation in HLA Class I-Negative Cancer Cells With Peptide-?2M Fusion Molecules", European Journal of Immunology, 31(2): 440-449, 2001. Abstract. p. 442, Fig. 1.

Toshitani et al. "Expression of a Single-Chain HLA Class I Molecule in a Human Cell Line: Presentation of Exogenous Peptide and Processed Antigen to Cytotoxic T Lymphocytes", Proc. Natl. Acad. Sci. USA, XP002051157, 93(1): 236-240, Jan. 1996. Abstract, p. 237, col. 2, Last §, Fig. 1, p. 236, col. 2, p. 237, col. 2, § 2 From the Bottom, p. 240, §1.

Uger et al "Covalent Linkage to ?2-Microglobulin Enhances the MHC Stability and Antigenicity of Suboptimal CTL Epitopes", The Journal of Immunology, 162: 6024-6028, 1999.

Uger et al. "Creating CTL Targets With Epitope-Linked Beta 2-Microglobulin Constructs", Journal of Immunology, XP002115504, 160(4): 1598-1605, Feb. 15, 1998.

Urban et al. "The Discovery and Use of IILA-Associated Epitopes as Drugs", Critical Reviews in Immunology, 17(5-6): 387-397, 1997.

Zajac et al. "Generation of Tumoricidal Cytotoxic T Lymphocytes From Healthy Donors, After In-Vitro Stimulation With a Replicatin-Incompetent Vaccina Virus Encoding Mart-1/Melan-A 27-35 Epitope", International Journal of Cancer, 71: 491-496, 1997.

Response Dated Sep. 22, 2011 to Examinees Report of Aug. 27, 2010 From the Australian Government, IP Australia Re. Application No. 2008243241.

Response Dated Oct. 2, 2011 to Communication Pursuant to Article 94(3) EPC of Mar. 24, 2011 From the European Patent Office Re. Application No. 07777164.0.

Response Dated Sep. 27, 2011 to Office Action of Jan. 27, 2011 From the Patent Office of the State Intellectual Porperty Office of the People's Republic of China Re. Application No. 200780018196.5.

Examiner's Report Dated Oct. 3, 2011 From the Australian Government, IP Australia Re. Application No. 2008243241.

Response Dated Sep. 27, 2011 to Examiner's Report of Aug. 27, 2010 From the Australian Government, IP Australia Re. Application No. 2008243241.

Supplementary Response Dated Oct. 4, 2011 to Examiner's Report of Aug. 27, 2010 From the Australian Government, IP Australia Re. Application No. 2008243241.

Examiner's Report Dated Oct. 13, 2011 From the Australian Government, IP Australia Re. Application No. 2008243241.

Response Dated Nov. 1, 2011 to Communication Pursuant to Rules (70(2) and 70a(2) EPC and Reference to Rule 39(1) EPC of May 10, 2011 From the European Patent Office Re. Application No. 10166544.6.

Response Dated Nov. 30, 2011 to Requisition by the Examiner of Jun. 7, 2011 From the Canadian Intellectual Property Office Re.: Application No. 2,404,489.

Translation of Official Letter of Inquiry Dated Nov. 15, 2011 From the Japanese Patent Office Re. Application No. 2003-504888.

Translation of Office Action Dated Jun. 5, 2012 From the Japanese Patent Office Re. Application No. 2009-512056.

Official Action Dated Nov. 16, 2012 From the US Patent and Trademark Office Re.: U.S. Appl. No. 12/486,794.

Requisition by the Examiner Dated Oct. 22, 2012 From the Canadian Intellectual Property Office Re.: Application No. 2,404,489.

Translation of Office Action Dated Jul. 2, 2012 From the Patent Office of the State Intellectual Property Office of the People's Republic of China Re. Application No. 200780018196.5.

Examination Report Dated Jul. 24, 2012 From the Instituto Mexicano de la Propiedad Industrial Re. Application No. MX/a/2008/014722 and Its Summary in English.

Formal Opinion Dated Oct. 31, 2012 From the Serviço Público Federal, Ministério do Desenvolvimento, Indústria e Comércio Exterior, Instituto Nacional da Propriedade Industrial do Brazil Re. Application No. PI0712716-2.

* cited by examiner

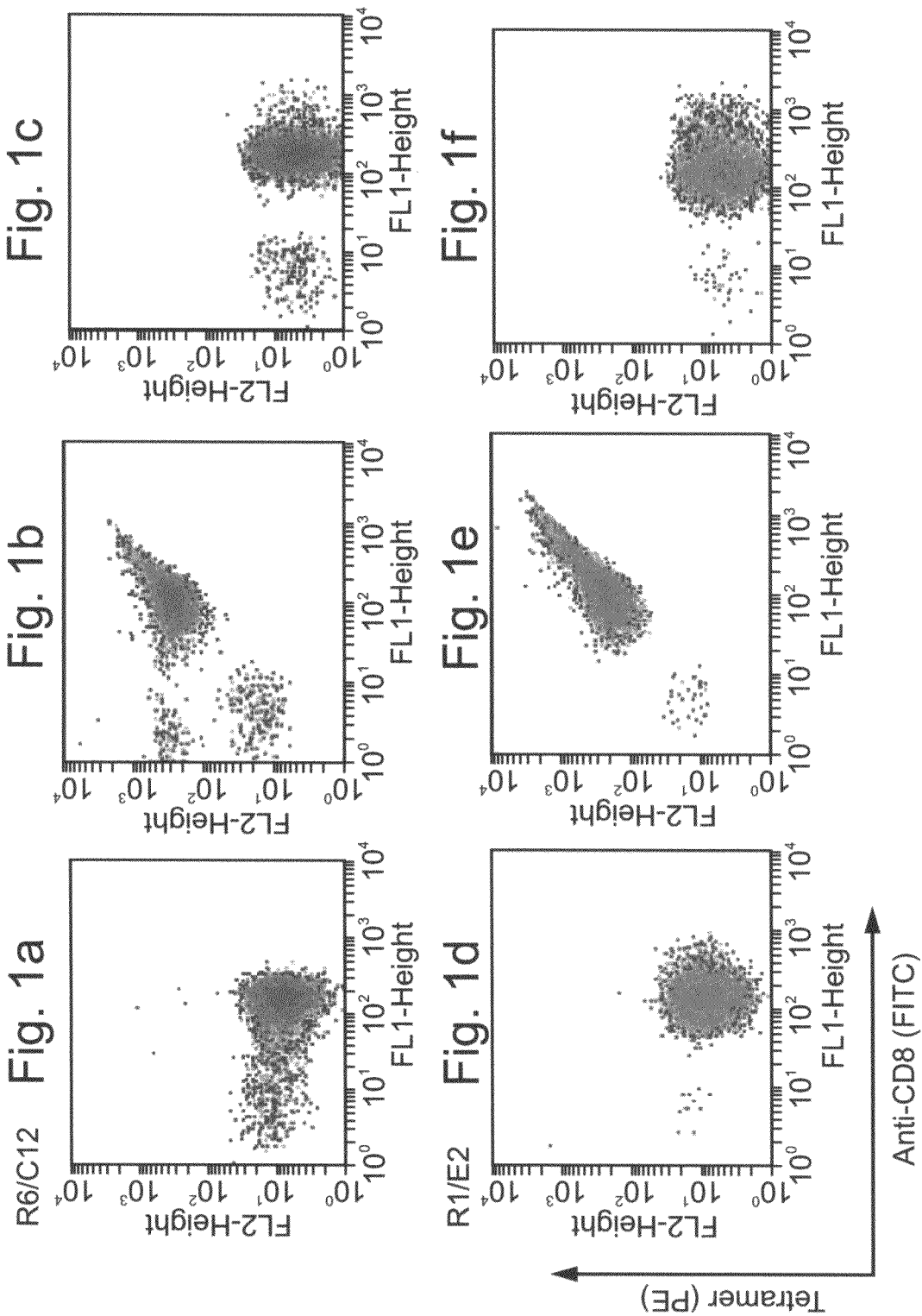

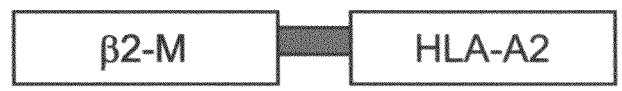

Fig. 1g

Nucleic Acid Sequence of ScHLA-A2 (SEQ ID NO:1)

ATGATCCAGCGTACTCCAAAGATTCAGGTTTACTCACGTCATCCAGCAGAGAATGGAAAGTCAAATTTC
CTGAATTGCTATGTGTCTGGGTTTCATCCATCCGACATTGAAGTTGACTTACTGAAGAATGGAGAGAGA
ATTGAAAAAGTGGAGCATTCAGACTTGTCTTTCAGCAAGGACTGGTCTTTCTATCTCTTGTATTATACT
GAgTTCACCCCCACTGAAAAAGATGAGTATGCCTGCCGTGTGAACCACGTGACTTTGTCACAGCCCAAG
ATAGTTAAGTGGGATCGAGACATGggtggcggtggaagcggcggtggaggctctggtggaggtggcagc
GGCTCTCACTCCATGAGGTATTTCTTCACATCCGTGTCCCGGCCCGGCCGCGGGGAGCCCCGCTTCATC
GCAGTGGGCTACGTGGACGACACGCAGTTCGTGCGGTTCGACAGCGACGCCGCGAGCCAGAGGATGGAG
CCGCGGGCGCCGTGGATAGAGCAGGAGGGTCCGGAGTATTGGGACGGGGAGACACGGAAAGTGAAGGCC
CACTCACAGACTCACCGAGTGGACCTGGGGACCCTGCGCGGCTACTACAACCAGAGCGAGGCCGGTTCT
CACACCGTCCAGAGGATGTATGGCTGCGACGTGGGGTCGGACTGGCGCTTCCTCCGCGGGTACCACCAG
TACGCCTACGACGGCAAGGATTACATCGCCCTGAAAGAGGACCTGCGCTCTTGGACCGCGGCGGACATG
GCAGCTCAGACCACCAAGCACAAGTGGGAGGCGGCCCATGTGGCGGAGCAGTTGAGAGCCTACCTGGAG
GGCACGTGCGTGGAGTGGCTCCGCAGATACCTGGAGAACGGGAAGGAGACGCTGCAGCGCACGGACGCC
CCCAAAACGCAcATGACTCACCACGCTGTCTCTGACCATGAAGCCACCCTGAGGTGCTGGGCCCTGAGC
TTCTACCCTGCGGAGATCACACTGACCTGGCAGCGGGATGGGGAGGACCAGACCCAGGACACGGAGCTC
GTGGAGACCAGGCCTGCAGGGGATGGAACCTTCCAGAAGTGGGCGGCTGTGGTGGTGCCTTCTGGACAG
GAGCAGAGATACACCTGCCATGTGCAGCATGAGGGTTTGCCCAAGCCCCTCACCCTGAGATGGGAG Amino acid Sequence of ScHLA-A2 (SEQ ID NO:2)

MIQRTPKIQVYSRHPAENGKSNFLNCYVSGFHPSDIEVDLLKNGERIEKVEHSDLSFSKDWSFYLLYYT
EFTPTEKDEYACRVNHVTLSQPKIVKWDRDMGGGGSGGGGSGGGGSGSHSMRYFFTSVSRPGRGEPRFI
AVGYVDDTQFVRFDSDAASQRMEPRAPWIEQEGPEYWDGETRKVKAHSQTHRVDLGTLRGYYNQSEAGS
HTVQRMYGCDVGSDWRFLRGYHQYAYDGKDYIALKEDLRSWTAADMAAQTTKHKWEAAHVAEQLRAYLE
GTCVEWLRRYLENGKETLQRTDAPKTHMTHHAVSDHEATLRWALSFYPAEITLTWQRDGEDQTQDTELV
ETRPAGDGTFQKWAAVVVPSGQEQRYTCHVQHEGLPKPLTLRWE

Fig. 1h

Nucleic Acid Sequence of B2M-aTacVL (SEQ ID NO:4)

```
ATGATCCAGCGTACTCCAAAGATTCAGGTTTACTCACGTCATCCAGCAGAGAATGGAAAGTCAAATTTC
CTGAATTGCTATGTGTCTGGGTTTCATCCATCCGACATTGAAGTTGACTTACTGAAGAATGGAGAGAGA
ATTGAAAAAGTGGAGCATTCAGACTTGTCTTTCAGCAAGGACTGGTCTTTCTATCTCTTGTATTATACT
GAgTTCACCCCCACTGAAAAAGATGAGTATGCCTGCCGTGTGAACCACGTGACTTTGTCACAGCCCAAG
ATAGTTAAGTGGGATCGAGACATGggtggcggtggaagcggcggtggaggctctggtggaggtggcagc
GGCTCTCACTCCATGAGGTATTTCTTCACATCCGTGTCCCGGCCCGCGGGGAGCCCCGCTTCATC
GCAGTGGGCTACGTGGACGACACGCAGTTCGTGCGGTTCGACAGCGACGCCGCGAGCCAGAGGATGGAG
CCGCGGGCGCCGTGGATAGAGCAGGAGGGTCCGGAGTATTGGGACGGGGAGACACGGAAAGTGAAGGCC
CACTCACAGACTCACCGAGTGGACCTGGGGACCCTGCGCGGCTACTACAACCAGAGCGAGGCCGGTTCT
CACACCGTCCAGAGGATGTATGGCTGCGACGTGGGGTCGGACTGGCGCTTCCTCCGCGGGTACCACCAG
TACGCCTACGACGGCAAGGATTACATCGCCCTGAAAGAGGACCTGCGCTCTTGGACCGCGGCGGACATG
GCAGCTCAGACCACCAAGCACAAGTGGGAGGCGGCCCATGTGGCGGAGCAGTTGAGAGCCTACCTGGAG
GGCACGTGCGTGGAGTGGCTCCGCAGATACCTGGAGAACGGGAAGGAGACGCTGCAGCGCACGGACGCC
CCCAAAACGCAcATGACTCACCACGCTGTCTCTGACCATGAAGCCACCCTGAGGTGCTGGGCCCTGAGC
TTCTACCCTGCGGAGATCACACTGACCTGGCAGCGGGATGGGGAGGACCAGACCCAGGACACGGAGCTC
GTGGAGACCAGGCCTGCAGGGGATGGAACCTTCCAGAAGTGGGCGGCTGTGGTGGTGCCTTCTGGACAG
GAGCAGAGATACACCTGCCATGTGCAGCATGAGGGTTTGCCCAAGCCCCTCACCCTGAGATGGGAGGgc
ggaggagggtccggtggcggaggttcaggaggcggtggatcgCAAATTGTTCTCACCCAGTCTCCAGCA
ATCATGTCTGCATCTCCAGGGGAGAAGGTCACCATAACCTGCAGTGCCAGCTCAAGTATAAGTTACATG
CACTGGTTCCAGCAGAAGCCAGGCACTTCTCCCAAACTCTGGATTTATACCACATCCAACCTGGCTTCT
GGAGTCCCTGCTCGCTTCAGTGGCAGTGGATCTGGGACCTCTTACTCTCTCACAATCAGCCGAATGGAG
GCTGAAGATGCTGCCACTTATTACTGCCATCAAAGGAGTACTTACCCACTCACGTTCGGTTgTGGtACC
AAGCTGGAGCTC
```

Amino Acid Sequence of B2M-aTacVL (SEQ ID NO:5)

```
MIQRTPKIQVYSRHPAENGKSNFLNCYVSGFHPSDIEVDLLKNGERIEKVEHSDLSFSKDWSFYLLYYT
EFTPTEKDEYACRVNHVTLSQPKIVKWDRDMGGGGSGGGGSGGGGSGSHSMRYFFTSVSRPGREPRFI
AVGYVDDTQFVRFDSDAASQRMEPRAPWIEQEGPEYWDGETRKVKAHSQTHRVDLGTLRGYYNQSEAGS
HTVQRMYGCDVGSDWRFLRGYHQYAYDGKDYIALKEDLRSWTAADMAAQTTKHKWEAAHVAEQLRAYLE
GTCVEWLRRYLENGKETLQRTDAPKTHMTHHAVSDHEATLRCWALSFYPAEITLTWQRDGEDQTQDTEL
VETRPAGDGTFQKWAAVVVPSGQEQRYTCHVQHEGLPKPLTLRWEGGGGSGGGGSGGGGSQIVLTQSPA
IMSASPGEKVTITCSASSSISYMHWFQQKPGTSPKLWIYTTSNLASGVPARFSGSGSGTSYSLTISRME
AEDAATYYCHQRSTYPLTFGCGTKLEL
```

Fig. 2e

Nucleic Acid Sequence of aTacVH (SEQ ID NO:6)

```
CAGGTCCAtCTGCAGCAGTCTGGGGCTGAACTGGCAAAACCTGGGGCCTCAGTGAAGATGTCCTGCAAG
GCTTCTGGCTACACCTTTACTAGCTACAGGATGCACTGGGTAAAACAGAGGCCTGGACAGGGTCTGGAA
TGGATTGGATATATTAATCCTAGCACTGGGTATACTGAATACAATCAGAAGTTCAAGGACAAGGCCACA
TTGACTGCAGACAAATCCTCCAGCACAGCCTACATGCAACTGAGCAGCCTGACATTTGAGGACTCTGCA
GTCTATTACTGTGCAAGAGGGGGGGGGTCTTTGACTACTGGGGCCAAGGAACCACTCTCACAGTCTCC
TCA
```

Amino Acid Sequence of aTacVH (SEQ ID NO:7)

```
QVHLQQSGAELAKPGASVKMSCKASGYTFTSYRMHWVKQRPGQGLEWIGYINPSTGYTEYNQKFKDKAT
LTADKSSSTAYMQLSSLTFEDSAVYYCARGGGVFDYWGQGTTLTVSS
```

Fig. 2f

```
                        SEQUENCE LISTING

<160> NUMBER OF SEQ ID NOS: 17

<210> SEQ ID NO 1
<211> LENGTH: 1170
<212> TYPE: DNA
<213> ORGANISM: Artificial sequence
<220> FEATURE:
<223> OTHER INFORMATION: scHLA-A2 construct nucleic acid sequence

<400> SEQUENCE: 1
atgatccagc gtactccaaa gattcaggtt tactcacgtc atccagcaga gaatggaaag      60
tcaaatttcc tgaattgcta tgtgtctggg tttcatccat ccgacattga agttgactta     120
ctgaagaatg gagagagaat tgaaaaagtg gagcattcag acttgtcttt cagcaaggac     180
tggtctttct atctcttgta ttatactgag ttcaccccca ctgaaaaaga tgagtatgcc     240
tgccgtgtga accacgtgac tttgtcacag cccaagatag ttaagtggga tcgagacatg     300
ggtggcggtg gaagcggcgg tggaggctct ggtggaggtg gcagcggctc tcactccatg     360
aggtatttct tcacatccgt gtcccggccc ggccgcgggg agcccgcgtt catcgcagtg     420
ggctacgtgg acgacacgca gttcgtgcgg ttcgacagcg acgccgcgag ccagaggatg     480
gagccgcggg cgccgtggat agagcaggag ggtccggagt attgggacgg ggagacacgg     540
aaagtgaagg cccactcaca gactcaccga gtggacctgg ggaccctgcg cggctactac     600
aaccagagcg aggccggttc tcacaccgtc cagaggatgt atggctgcga cgtggggtcg     660
gactggcgct tcctccgcgg gtaccaccag tacgcctacg acggcaagga ttacatcgcc     720
ctgaaagagg acctgcgctc ttggaccgcg gcggacatgg cagctcagac caccaagcac     780
aagtgggagg cggcccatgt ggcggagcag ttgagagcct acctggaggg cacgtgcgtg     840
gagtggctcc gcagatacct ggagaacggg aaggagacgc tgcagcgcac ggacgccccc     900
aaaacgcaca tgactcacca cgctgtctct gaccatgaag ccaccctgag gtgctgggcc     960
ctgagcttct accctgcgga gatcacactg acctggcagc gggatgggga ggaccagacc    1020
caggacacgg agctcgtgga gaccaggcct gcagggatg gaaccttcca gaagtgggcg    1080
gctgtggtgg tgccttctgg acaggagcag agatacacct gccatgtgca gcatgagggt    1140
```

```
ttgcccaagc ccctcaccct gagatgggag                                         1170
```

<210> SEQ ID NO 2
<211> LENGTH: 389
<212> TYPE: PRT
<213> ORGANISM: Artificial sequence
<220> FEATURE:
<223> OTHER INFORMATION: scHLA-A2 amino acid product sequence

<400> SEQUENCE: 2

```
Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met Gly Gly Gly Ser Gly Gly Gly Ser Gly Gly
            100                 105                 110

Gly Gly Ser Gly Ser His Ser Met Arg Tyr Phe Phe Thr Ser Val Ser
        115                 120                 125

Arg Pro Gly Arg Gly Glu Pro Arg Phe Ile Ala Val Gly Tyr Val Asp
    130                 135                 140

Asp Thr Gln Phe Val Arg Phe Asp Ser Asp Ala Ala Ser Gln Arg Met
145                 150                 155                 160

Glu Pro Arg Ala Pro Trp Ile Glu Gln Glu Gly Pro Glu Tyr Trp Asp
                165                 170                 175

Gly Glu Thr Arg Lys Val Lys Ala His Ser Gln Thr His Arg Val Asp
            180                 185                 190

Leu Gly Thr Leu Arg Gly Tyr Tyr Asn Gln Ser Glu Ala Gly Ser His
        195                 200                 205

Thr Val Gln Arg Met Tyr Gly Cys Asp Val Gly Ser Asp Trp Arg Phe
    210                 215                 220

Leu Arg Gly Tyr His Gln Tyr Ala Tyr Asp Gly Lys Asp Tyr Ile Ala
225                 230                 235                 240

Leu Lys Glu Asp Leu Arg Ser Trp Thr Ala Ala Asp Met Ala Ala Gln
                245                 250                 255

Thr Thr Lys His Lys Trp Glu Ala Ala His Val Ala Glu Gln Leu Arg
            260                 265                 270

Ala Tyr Leu Glu Gly Thr Cys Val Glu Trp Leu Arg Arg Tyr Leu Glu
        275                 280                 285

Asn Gly Lys Glu Thr Leu Gln Arg Thr Asp Ala Pro Lys Thr His Met
    290                 295                 300

Thr His His Ala Val Ser Asp His Glu Ala Thr Leu Arg Trp Ala Leu
305                 310                 315                 320

Ser Phe Tyr Pro Ala Glu Ile Thr Leu Thr Trp Gln Arg Asp Gly Glu
                325                 330                 335

Asp Gln Thr Gln Asp Thr Glu Leu Val Glu Thr Arg Pro Ala Gly Asp
            340                 345                 350

Gly Thr Phe Gln Lys Trp Ala Ala Val Val Val Pro Ser Gly Gln Glu
```

355                 360                 365
Gln Arg Tyr Thr Cys His Val Gln His Glu Gly Leu Pro Lys Pro Leu
        370                 375                 380

Thr Leu Arg Trp Glu
385

<210> SEQ ID NO 3
<211> LENGTH: 15
<212> TYPE: PRT
<213> ORGANISM: Artificial sequence
<220> FEATURE:
<223> OTHER INFORMATION: 'Single chain' construct, amino acid linker

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 1530
<212> TYPE: DNA
<213> ORGANISM: Artificial sequence
<220> FEATURE:
<223> OTHER INFORMATION: B2M-aTacVL construct nucleic acid sequence

<400> SEQUENCE: 4

```
atgatccagc gtactccaaa gattcaggtt tactcacgtc atccagcaga gaatggaaag      60
tcaaatttcc tgaattgcta tgtgtctggg tttcatccat ccgacattga agttgactta     120
ctgaagaatg gagagagaat tgaaaaagtg gagcattcag acttgtcttt cagcaaggac     180
tggtctttct atctcttgta ttatactgag ttcacccccca ctgaaaaaga tgagtatgcc    240
tgccgtgtga accacgtgac tttgtcacag cccaagatag ttaagtggga tcgagacatg    300
ggtggcggtg aagcggcgg tggaggctct ggtggaggtg gcagcggctc tcactccatg     360
aggtatttct tcacatccgt gtcccggccc ggccgcgggg agcccgcctt catcgcagtg    420
ggctacgtgg acgacacgca gttcgtgcgg ttcgacagcg acgccgcgag ccagaggatg    480
gagccgcggg cgccgtggat agagcaggag ggtccggagt attgggacgg ggagacacgg   540
aaagtgaagg cccactcaca gactcaccga gtggacctgg ggaccctgcg cggctactac   600
aaccagagcg aggccggttc tcacaccgtc cagaggatgt atggctgcga cgtggggtcg   660
gactggcgct tcctccgcgg gtaccaccag tacgcctacg acggcaagga ttacatcgcc   720
ctgaaagagg acctgcgctc ttggaccgcg gcggacatgg cagctcagac caccaagcac   780
aagtgggagg cggcccatgt ggcggagcag ttgagagcct acctggaggg cacgtgcgtg   840
gagtggctcc gcagatacct ggagaacggg aaggagacgc tgcagcgcac ggacgccccc   900
aaaacgcaca tgactcacca cgctgtctct gaccatgaag ccaccctgag gtgctgggcc   960
ctgagcttct accctgcgga gatcacactg acctggcagc gggatgggga ggaccagacc   1020
caggacacgg agctcgtgga gaccaggcct gcaggggatg gaaccttcca gaagtgggcg   1080
gctgtggtgg tgccttctgg acaggagcag agatacacct gccatgtgca gcatgagggt   1140
ttgcccaagc ccctcaccct gagatgggag gcgaggag ggtccggtgg cggaggttca   1200
ggaggcggtg gatcgcaaat tgttctcacc cagtctccag caatcatgtc tgcatctcca   1260
ggggagaagg tcaccataac ctgcagtgcc agctcaagta taagttacat gcactggttc   1320
cagcagaagc caggcacttc tcccaaactc tggatttata ccacatccaa cctggcttct   1380
ggagtccctg ctcgcttcag tggcagtgga tctgggacct cttactctct cacaatcagc   1440
cgaatggagg ctgaagatgc tgccacttat tactgccatc aaaggagtac ttacccactc   1500
```
acgttcggtt gtggtaccaa gctggagctc                          1530

<210> SEQ ID NO 5
<211> LENGTH: 510
<212> TYPE: PRT
<213> ORGANISM: Artificial sequence
<220> FEATURE:
<223> OTHER INFORMATION: B2M-aTacVL construct amino acid product
      sequence

<400> SEQUENCE: 5

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met Gly Gly Gly Gly Ser Gly Gly Gly Gly Ser Gly Gly
            100                 105                 110

Gly Gly Ser Gly Ser His Ser Met Arg Tyr Phe Phe Thr Ser Val Ser
        115                 120                 125

Arg Pro Gly Arg Gly Glu Pro Arg Phe Ile Ala Val Gly Tyr Val Asp
    130                 135                 140

Asp Thr Gln Phe Val Arg Phe Asp Ser Asp Ala Ala Ser Gln Arg Met
145                 150                 155                 160

Glu Pro Arg Ala Pro Trp Ile Glu Gln Glu Gly Pro Glu Tyr Trp Asp
                165                 170                 175

Gly Glu Thr Arg Lys Val Lys Ala His Ser Gln Thr His Arg Val Asp
            180                 185                 190

Leu Gly Thr Leu Arg Gly Tyr Tyr Asn Gln Ser Glu Ala Gly Ser His
        195                 200                 205

Thr Val Gln Arg Met Tyr Gly Cys Asp Val Gly Ser Asp Trp Arg Phe
    210                 215                 220

Leu Arg Gly Tyr His Gln Tyr Ala Tyr Asp Gly Lys Asp Tyr Ile Ala
225                 230                 235                 240

Leu Lys Glu Asp Leu Arg Ser Trp Thr Ala Ala Asp Met Ala Ala Gln
                245                 250                 255

Thr Thr Lys His Lys Trp Glu Ala Ala His Val Ala Glu Gln Leu Arg
            260                 265                 270

Ala Tyr Leu Glu Gly Thr Cys Val Glu Trp Leu Arg Arg Tyr Leu Glu
        275                 280                 285

Asn Gly Lys Glu Thr Leu Gln Arg Thr Asp Ala Pro Lys Thr His Met
    290                 295                 300

Thr His His Ala Val Ser Asp His Glu Ala Thr Leu Arg Cys Trp Ala
305                 310                 315                 320

Leu Ser Phe Tyr Pro Ala Glu Ile Thr Leu Thr Trp Gln Arg Asp Gly
                325                 330                 335

Glu Asp Gln Thr Gln Asp Thr Glu Leu Val Glu Thr Arg Pro Ala Gly
            340                 345                 350

```
Asp Gly Thr Phe Gln Lys Trp Ala Ala Val Val Pro Ser Gly Gln
            355                 360                 365

Glu Gln Arg Tyr Thr Cys His Val Gln His Glu Gly Leu Pro Lys Pro
370                 375                 380

Leu Thr Leu Arg Trp Glu Gly Gly Gly Ser Gly Gly Gly Gly Ser
385                 390                 395                 400

Gly Gly Gly Gly Ser Gln Ile Val Leu Thr Gln Ser Pro Ala Ile Met
                405                 410                 415

Ser Ala Ser Pro Gly Glu Lys Val Thr Ile Thr Cys Ser Ala Ser Ser
            420                 425                 430

Ser Ile Ser Tyr Met His Trp Phe Gln Gln Lys Pro Gly Thr Ser Pro
        435                 440                 445

Lys Leu Trp Ile Tyr Thr Thr Ser Asn Leu Ala Ser Gly Val Pro Ala
450                 455                 460

Arg Phe Ser Gly Ser Gly Ser Gly Thr Ser Tyr Ser Leu Thr Ile Ser
465                 470                 475                 480

Arg Met Glu Ala Glu Asp Ala Ala Thr Tyr Tyr Cys His Gln Arg Ser
                485                 490                 495

Thr Tyr Pro Leu Thr Phe Gly Cys Gly Thr Lys Leu Glu Leu
            500                 505                 510

<210> SEQ ID NO 6
<211> LENGTH: 348
<212> TYPE: DNA
<213> ORGANISM: Artificial sequence
<220> FEATURE:
<223> OTHER INFORMATION: aTacVH sequence - a part of the B2M-aTac(dsFv)
      construct sequence

<400> SEQUENCE: 6
caggtccatc tgcagcagtc tggggctgaa ctggcaaaac ctggggcctc agtgaagatg      60
tcctgcaagg cttctggcta cacctttact agctacagga tgcactgggt aaaacagagg     120
cctggacagg gtctggaatg gattggatat attaatccta gcactgggta tactgaatac     180
aatcagaagt tcaaggacaa ggccacattg actgcagaca atcctccag cacagcctac     240 atgcaactga gcagcctgac atttgaggac tctgcagtct attactgtgc aagagggggg     300
ggggtctttg actactgggg ccaaggaacc actctcacag tctcctca                  348

<210> SEQ ID NO 7
<211> LENGTH: 116
<212> TYPE: PRT
<213> ORGANISM: Artificial sequence
<220> FEATURE:
<223> OTHER INFORMATION: aTacVH amino acid sequence-a part of the
      B2M-aTac(dsFv) encoded protein

<400> SEQUENCE: 7

Gln Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Arg Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
```

```
                     85                  90                  95

Ala Arg Gly Gly Gly Val Phe Asp Tyr Trp Gly Gln Gly Thr Thr Leu
                100                 105                 110

Thr Val Ser Ser
        115

<210> SEQ ID NO 8
<211> LENGTH: 9
<212> TYPE: PRT
<213> ORGANISM: Artificial sequence
<220> FEATURE:
<223> OTHER INFORMATION: HLA-A2-restricted synthetic peptide, derived
      from the melanoma differentiation antigen gp100

<400> SEQUENCE: 8

Ile Met Asp Gln Val Pro Phe Ser Val
1               5

<210> SEQ ID NO 9
<211> LENGTH: 9
<212> TYPE: PRT
<213> ORGANISM: Artificial sequence
<220> FEATURE:
<223> OTHER INFORMATION: HLA-A2-restricted synthetic peptide, derived
      from the melanoma differentiation antigen gp100

<400> SEQUENCE: 9

Tyr Leu Glu Pro Gly Pro Val Thr Val
1               5

<210> SEQ ID NO 10
<211> LENGTH: 9
<212> TYPE: PRT
<213> ORGANISM: Artificial sequence
<220> FEATURE:
<223> OTHER INFORMATION: HTLV-1 virus derived synthetic peptide

<400> SEQUENCE: 10

Leu Leu Phe Gly Tyr Pro Val Tyr Val
1               5

<210> SEQ ID NO 11
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 11
ggaagcgttg gcgcatatga tccagcgtac tcc                                33

<210> SEQ ID NO 12
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 12
tcctgaacct ccgccaccgg accctcctcc gccctcccat ctcagggt                 48

<210> SEQ ID NO 13
<211> LENGTH: 48
<212> TYPE: DNA
<213> ORGANISM: Artificial sequence
<220> FEATURE:
<223> OTHER INFORMATION: Single strand DNA oligonucleotide
```

```
<400> SEQUENCE: 13
tccggtggcg gaggttcagg aggcggtgga tcgcaaattg ttctcacc          48

<210> SEQ ID NO 14
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 14
gcagtaagga attcattaga gctccagctt ggt                         33

<210> SEQ ID NO 15
<211> LENGTH: 45
<212> TYPE: DNA
<213> ORGANISM: Artificial sequence
<220> FEATURE:
<223> OTHER INFORMATION: Oligonucleotide, encoding the single chain
      construct linker

<400> SEQUENCE: 15
ggcggaggag ggtccggtgg cggaggttca ggaggcggtg gatcg            45

<210> SEQ ID NO 16
<211> LENGTH: 9
<212> TYPE: PRT
<213> ORGANISM: Artificial sequence
<220> FEATURE:
<223> OTHER INFORMATION: Influenza virus derived MHC-restricted peptide

<400> SEQUENCE: 16

Gly Ile Leu Gly Phe Val Phe Thr Leu
1               5

<210> SEQ ID NO 17
<211> LENGTH: 9
<212> TYPE: PRT
<213> ORGANISM: Artificial sequence
<220> FEATURE:
<223> OTHER INFORMATION: Hepititis B virus derived MHC-restricted
      peptide

<400> SEQUENCE: 17

Ser Thr Asn Arg Gln Ser Gly Arg Gln
1               5
```

IMMUNO-MOLECULES CONTAINING VIRAL PROTEINS, COMPOSITIONS THEREOF AND METHODS OF USING

RELATED APPLICATIONS

This application is a divisional of U.S. patent application Ser. No. 10/482,532 filed on Sep. 17, 2004, which is a National Phase of PCT Patent Application No. PCT/IL02/00478 filed on Jun. 18, 2002, which is a continuation of U.S. patent application Ser. No. 10/108,511 filed on Mar. 29, 2002, now abandoned, which claims the benefit of priority of U.S. Provisional Patent Application No. 60/298,915 filed on Jun. 19, 2001. The contents of the above applications are all incorporated herein by reference.

FIELD AND BACKGROUND OF THE INVENTION

The present invention relates to a novel concept in immunotherapy, by which deception of the immune system results in specific and most efficient destruction of cells of interest, cancer cells in particular.

There is strong evidence that tumor progression in cancer patients is controlled by the immune system. This conclusion is based on observations that tumor progression is often associated with secretion of immune suppressive factors and/or downregulation of MHC class I antigen presentation functions (1-5). The inference is that tumors must have elaborated strategies to circumvent an apparently effective immune response. Importantly, a tumor-specific immune response can be detected in individuals (6-8).

The apparent inefficiency of anti tumor immune responses that results in failure to combat the disease laid the foundation to current concepts of immunotherapy. It is suggested that boosting the anti-tumor immune response by deliberate vaccination or by other immunotherapeutic approaches may increase the potential benefits of immune-based therapies (6, 9-11).

The MHC class I-restricted CD8 cytotoxic T cell (CTL) effector arm of the adaptive immune response is best equipped to recognize the tumor as foreign and initiate the cascade of events resulting in tumor destruction (12,13). Therefore, the most attractive approach in cancer immunotherapy is centered on vaccination strategies designed to enhance the CTL arm of the antitumor response and consequently overcome the mechanisms of tumor escape from CTL (9-11).

One of the best-studied escape mechanisms by which tumor cells evade immune attack is by downregulation of the MHC class I molecules which are the antigens recognized by CTLs (1-5,14).

Mutations along the class I presentation pathway should be the simplest way for tumors to escape CTL-mediated elimination since it can be achieved by one or two mutational events (two mutations to inactivate both alleles or one mutation to create a dominant negative inhibitor) (1-3).

Downregulation of MHC class I expression is frequently observed in human tumors, and is particularly pronounced in metastatic lesions (3, 14-17). This is circumstantial but nevertheless compelling evidence of the role of CTL in controlling tumor progression in cancer patients. MHC class I expression has been mainly analyzed in surgically removed tumor specimens using immunohistochemical methods (14-15). Partial reduction or complete loss of MHC have been reported, encompassing all MHC molecules or limited to particular alleles (14-15). MHC loss can be seen in some but not all lesions of the same patient. Downregulation of MHC class I expression has been attributed to mutations in β2-microglobulin ((β2-m), transporter associated with antigen presentation (TAP) proteins, or the proteosomal LMP-2 and LMP-7 proteins (2, 18-21). Additional evidence implicating loss of MHC class I expression as a mechanism for tumor escape from CTL-mediated elimination comes from a longitudinal study of a melanoma patient. Tumor cells removed during initial surgery presented nine different antigens restricted to four separate HLA class I alleles to CTL clones established from the patient (1). The patient remained disease free for 5 years after which a metastasis was detected. Notably, a cell line established from the metastatic lesion had lost all four alleles that had previously been shown to present melanoma antigens.

Thus, the downregulation of class I MHC molecule is a severe limiting problem for cancer immunotherapy and the application of anti-cancer vaccines. There is thus a widely recognized need for, and it would be highly advantageous to have, an novel approach of immunotherapy devoid of the above limitations, namely an approach of immunotherapy which is independent of the level of expression of MHC class I molecules by cancer cells.

SUMMARY OF THE INVENTION

The MHC class I-restricted CD8 cytotoxic T cell (CTL) effector arm of the adaptive immune response is best equipped to recognize tumor cells as foreign and initiate the cascade of events resulting in tumor destruction. However, tumors have developed sophisticated strategies to escape immune effector mechanisms, of which the best-studied is by downregulation of MHC class I molecules which are the antigens recognized by CTLs.

To overcome this and develop new approaches for immunotherapy, and while reducing the present invention to practice, a recombinant molecule was constructed in which a single-chain MHC is specifically targeted to tumor cells through its fusion to cancer specific-recombinant antibody fragments or a ligand that binds to receptors expressed by tumor cells. As an exemplary molecule of the present invention, a single-chain HLA-A2 molecule was genetically fused to the variable domains of an anti IL-2 receptor α subunit-specific humanized antibody, anti-Tac (aTac). The construct, termed B2M-aTac(dsFv) was expressed in E. coli and functional molecules were produced by in vitro refolding in the presence of HLA-A2-restricted antigenic peptides. Flow cytometry studies revealed the ability to decorate antigen-positive, HLA-A2-negative human tumor cells with HLA-A2-peptide complexes in a manner that was entirely dependent upon the specificity of the targeting antibody fragment. Most importantly, B2M-aTac(dsFv)-mediated coating of target tumor cells made them susceptible for efficient and specific HLA-A2-restricted, melanoma gp100 peptide-specific CTL-mediated lysis. These results demonstrate the concept that antibody-guided tumor antigen-specific targeting of MHC-peptide complexes on tumor cells can render them susceptible and potentiate CTL killing. This novel approach now opens the way for the development of new immounotherapeutic strategies based on antibody targeting of natural cognate MHC ligands and CTL-based cytotoxic mechanisms.

Hence, while reducing the present invention to practice a novel strategy was developed to re-target class I MHC-peptide complexes on the surface of tumor cells in a way that is independent of the extent of class I MHC expression by the target tumor cells. To this end, in one embodiment of the present invention, two arms of the immune system were employed in fusion. One arm, the targeting moiety, comprises tumor-specific recombinant fragments of antibodies directed to tumor or differentiation antigens which have been used for many years to target radioisotopes, toxins or drugs to cancer cells (22, 23). The second, effector arm, is a single-chain MHC molecule (scMHC) composed of human β2-microglobulin linked to the three extracellular domains of the HLA-A2 heavy chain (24, 25, WO 01/72768). By connecting the two molecules into a single recombinant gene and expressing the gene. The new molecule is expressed efficiently in *E. coli* and produced, for example, by in vitro refolding in the presence of HLA-A2-restricted peptides. This approach, as shown herein, renders the target tumor cells susceptible to lysis by cytotoxic T cells regardless of their MHC expression level and thus may be employed as a new approach to potentiate CTL-mediated anti-tumor immunity. This novel approach will lead to the development of a new class of recombinant therapeutic agents capable of selective killing and elimination of tumor cells utilizing natural cognate MHC ligands and CTL-based cytotoxic mechanisms.

According to one aspect of the present invention there is provided an immuno-molecule comprising: a soluble human MHC class I effector domain; and a targeting domain being linked to the soluble human MHC class I effector domain.

Thus, according to another aspect of the present invention there is provided a nucleic acid construct encoding an immuno-molecule, the construct comprising: a first polynucleotide encoding a soluble human MHC class I effector domain; and a second polynucleotide encoding a targeting domain; the first polynucleotide and the second polynucleotide are selected and being joined such that the soluble human MHC class I effector domain and the antibody targeting domain are translationally fused optionally via a peptide linker in-between.

According to still another aspect of the present invention there is provided a nucleic acid construct encoding an immuno-molecule, the construct comprising: a first polynucleotide encoding a soluble human MHC class I effector domain; and a second polynucleotide encoding a variable region of one of a light chain or a heavy chain of an antibody targeting domain; the first polynucleotide and the second polynucleotide are selected and being joined such that the soluble human MHC class I effector domain and the variable region of the one of the light chain and heavy chain of the antibody targeting domain are translationally fused optionally via a peptide linker in-between; and a third polynucleotide encoding the other of the one of the light chain and heavy chain of the antibody targeting domain.

According to an additional aspect of the present invention there is provided a nucleic acid construct system comprising: a first nucleic acid construct which comprises: a first polynucleotide encoding a soluble human MHC class I effector domain; and a second polynucleotide encoding a variable region of one of a light chain or a heavy chain of an antibody targeting domain; the first polynucleotide and the second polynucleotide are selected and being joined such that the soluble human MHC class I effector domain and the variable region of the one of the light chain and heavy chain of the antibody targeting domain are translationally fused optionally via a peptide linker in-between; a second nucleic acid construct which comprises: a third polynucleotide encoding the other of the one of the light chain and heavy chain of the antibody targeting domain.

According to a further aspect of the present invention there is provided a method of selectively killing a cell in a patient, the cell presenting an antigen (e.g., a receptor), the method comprising administering to the patient an immuno-molecule which comprises: a soluble human MHC class I effector domain complexed with an MHC-restricted peptide; and a targeting domain being linked to the soluble human MHC class I effector domain, the targeting domain being for selectively binding to the antigen; whereby, the soluble human MHC class I effector domain complexed with the MHC-restricted peptide initiates a CTL mediated immune response against the cell, thereby selectively killing the cell in vivo.

According to further features in preferred embodiments of the invention described below, the targeting domain is an antibody targeting domain.

According to still further features in the described preferred embodiments the targeting domain is a ligand targeting domain.

According to still further features in the described preferred embodiments the ligand targeting domain is selected from the group consisting of PDGF, EGF, KGF, TGF, IL-2, IL-3, IL-4, IL-6, VEGF and its derivatives, TNF.

According to still further features in the described preferred embodiments the soluble human MHC class I effector domain and the antibody targeting domain are translationally fused, optionally with a translationally fused peptide linker in-between.

According to still further features in the described preferred embodiments the antibody targeting domain comprises a variable region of a light chain of an antibody linked to the effector domain.

According to still further features in the described preferred embodiments the variable region of the light chain of the antibody and the effector domain are translationally fused, optionally with a translationally fused peptide linker in-between.

According to still further features in the described preferred embodiments the antibody targeting domain further comprises a variable region of a heavy chain of an antibody linked to the variable region of the light chain of the antibody.

According to still further features in the described preferred embodiments the variable region of the heavy chain of the antibody and the variable region of the light chain of the antibody are translationally fused, optionally with a translationally fused peptide linker in-between.

According to still further features in the described preferred embodiments the variable region of the heavy chain of the antibody is linked to the variable region of the light chain of the antibody via a peptide linker.

According to still further features in the described preferred embodiments the variable region of the heavy chain of the antibody is linked to the variable region of the light chain of the antibody via at least one S—S bond.

According to still further features in the described preferred embodiments the antibody targeting domain comprises a variable region of a heavy chain of an antibody linked to the effector domain.

According to still further features in the described preferred embodiments the variable region of the heavy chain of the antibody and the effector domain are translationally fused, optionally with a translationally fused peptide linker in-between.

According to still further features in the described preferred embodiments the antibody targeting domain further comprises a variable region of a light chain of an antibody linked to the variable region of the heavy chain of the antibody.

According to still further features in the described preferred embodiments the variable region of the light chain of the antibody and the variable region of the heavy chain of the antibody are translationally fused, optionally with a translationally fused peptide linker in-between.

According to still further features in the described preferred embodiments the variable region of the light chain of the antibody is linked to the variable region of the heavy chain of the antibody via a peptide linker.

According to still further features in the described preferred embodiments the variable region of the light chain of the antibody is linked to the variable region of the heavy chain of the antibody via at least one S—S bond.

According to still further features in the described preferred embodiments the antibody targeting domain is capable of binding to a tumor associated antigen.

According to still further features in the described preferred embodiments the antibody targeting domain is capable of binding to a tumor specific antigen.

According to still further features in the described preferred embodiments the soluble human MHC class I effector domain comprises a functional human β-2 microglobulin and a functional human MHC class I heavy chain linked thereto.

According to still further features in the described preferred embodiments the functional human MHC class I heavy chain comprises domains α1-3.

According to still further features in the described preferred embodiments the functional human β-2 microglobulin and the functional human MHC class I heavy chain are translationally fused, optionally with a translationally fused peptide linker in-between.

According to still further features in the described preferred embodiments the soluble human MHC class I effector domain further comprises a MHC-restricted peptide.

According to still further features in the described preferred embodiments the MHC-restricted peptide is linked to the functional human β-2 microglobulin.

According to still further features in the described preferred embodiments the MHC-restricted peptide and the functional human β-2 microglobulin are translationally fused, optionally with a translationally fused peptide linker in-between.

According to still further features in the described preferred embodiments the MHC-restricted peptide is complexed with the functional human MHC class I heavy chain.

According to still further features in the described preferred embodiments the MHC-restricted peptide is derived from a common pathogen.

According to still further features in the described preferred embodiments the MHC-restricted peptide is derived from a pathogen for which there is an active vaccination.

According to still further features in the described preferred embodiments the MHC-restricted peptide is derived from a tumor associated or specific antigen.

According to further features in preferred embodiments of the invention described below, any of the nucleic acid constructs described herein, further comprising at least one cis acting regulatory sequence operably linked to the coding polynucleotides therein.

According to still further features in the described preferred embodiments the cis acting regulatory sequence is functional in bacteria.

According to still further features in the described preferred embodiments the cis acting regulatory sequence is functional in yeast.

According to still further features in the described preferred embodiments the cis acting regulatory sequence is functional in animal cells.

According to still further features in the described preferred embodiments the cis acting regulatory sequence is functional in plant cells.

According to still another aspect of the present invention there is provided a transformed cell comprising any of the nucleic acid constructs or the nucleic acid construct system described herein.

According to further features in preferred embodiments of the invention described below, the cell is a eukaryotic cell selected from the group consisting of a mammalian cell, an insect cell, a plant cell, a yeast cell and a protozoa cell.

According to still further features in the described preferred embodiments the cell is a bacterial cell.

According to yet an additional aspect of the present invention there is provided an isolated preparation of bacterial derived inclusion bodies comprising over 30 percent by weight of an immuno-molecule as described herein According to still an additional aspect of the present invention there is provided a method of producing an immuno-molecule comprising: expressing, in bacteria, the immuno-molecule which comprises: a soluble human MHC class I effector domain which includes a functional human β-2 microglobulin and a functional human MHC class I heavy chain linked thereto; and a targeting domain being linked to the soluble human MHC class I effector domain; and isolating the immuno-molecule.

According to further features in preferred embodiments of the invention described below, immuno-molecule further comprises an MHC-restricted peptide linked to the functional human β-2 microglobulin, the method further comprising refolding the immuno-molecule to thereby generate an MHC class I-MHC-restricted peptide complex.

According to still further features in the described preferred embodiments isolating the immuno-molecule is via size exclusion chromatography.

According to still further features in the described preferred embodiments an MHC-restricted peptide is co-expressed along with the immuno-molecule in the bacteria.

According to still further features in the described preferred embodiments expressing, in the bacteria, the immuno-molecule is effected such that the immuno-molecule forms inclusion bodies in the bacteria.

According to still further features in the described preferred embodiments the MHC-restricted peptide and the immuno-molecule co-form inclusion bodies in the bacteria.

According to still further features in the described preferred embodiments isolating the immuno-molecule further comprises: denaturing the inclusion bodies so as to release protein molecules therefrom; and renaturing the protein molecules.

According to still further features in the described preferred embodiments renaturing the protein molecules is effected in the presence of an MHC-restricted peptide.

According to still further features in the described preferred embodiments the MHC-restricted peptide is co-expressed in the bacteria.

The present invention successfully addresses the shortcomings of the presently known configurations by providing a new means with which to combat cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-F demonstrate binding of in vitro refolded scHLA-A2 complexes to CTLs. Melanoma differentiation antigen gp100-specific CTL clones R6C12 and R1E2 were reacted with in vitro refolded purified scHLA-A2 tetramers containing the G9-209M epitope recognized by R6C12 CTLs and G9-280V peptide recognized by R1E2 CTLs. CTLs were stained with FITC-anti-CD8 (FIGS. 1A and 1D), with PE-labeled scHLA-A2/G9-209M tetramers (FIGS. 1B and 1F) and with scHLA-A2/G9-280V tetramers (FIGS. 1C and 1E). R6C12 and R1E2 CTLs were stained with the specific G9-209M and G9-280V tetramer, respectively but not with control tetramer.

FIG. 1G is a schematic representation of a scHLA-A2 complex used in the experiments described under FIGS. 1A-F.

FIG. 1H demonstrates the nucleic (SEQ ID NO:1) and amino (SEQ ID NO:2) acid sequences of the scHLA-A2 schematically illustrated in FIG. 1G.

Figure 2A:
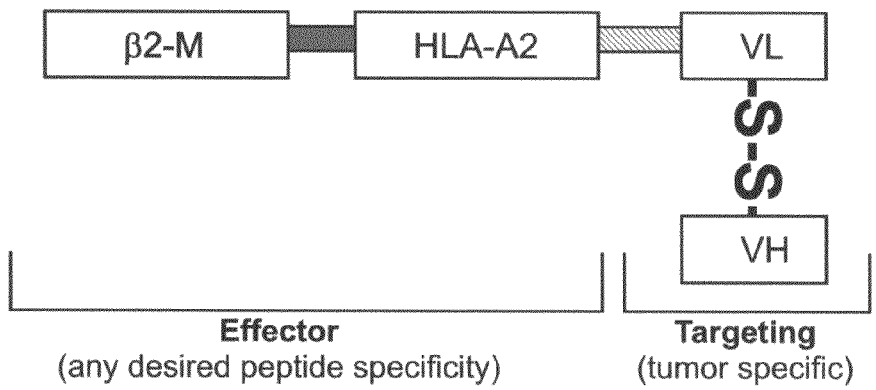
Figure 2B:
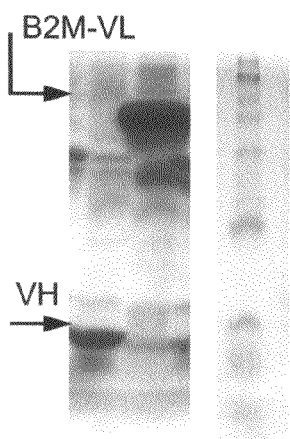
Figure 2C:
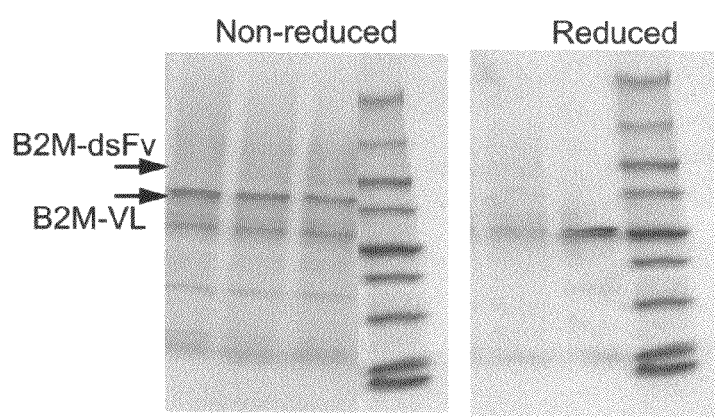
Figure 2D:
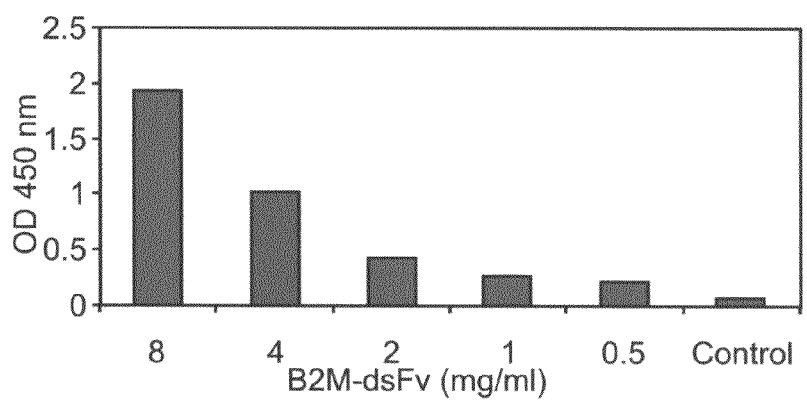

FIGS. 2A-D demonstrate the design, expression, purification and biochemical characterization of B2M-aTac(dsFv). FIG. 2A—The B2M-aTac(dsFv) construct was generated by fusing a single-chain MHC to an antibody variable Fv fragment. In the single-chain HLA-A2 gene, the human α-2m was fused to the three extracellular domains of HLA-A2 via a flexible 15-amino acid long linker [$(Gly_4-Ser)_3$, i.e., GGGGSGGGGSGGGGS (SEQ ID NO:3), encoded by GGCGGAGGAGGGTCCGGTGGCGGAGG TTCAG-GAGGCGGTGGATCG (SEQ ID NO:15)]. The same peptide linker was used to connect the scHLA gene to the antibody Fv fragment. The VL variable domain of the antibody was fused to the C-terminus of the scHLA-A2 gene while the VH variable domain was expressed separately. The two plasmids were expressed in separate cultures and the solubilized, reduced inclusion bodies were combined to form a disulfide-stabilized Fv fragments (dsFv) in which the Fv variable domains are stabilized by interchain disulfide bonds engineered between conserved framework residues. FIG. 2B shows SDS-PAGE analysis of the inclusion bodies from bacterial cultures induced to express the components of the B2M-aTac(dsFv); B2M-aTacVL and aTacVH. FIG. 3C shows SDS-PAGE analyses on non-reducing and reducing gels of B2M-aTac(dsFv) after ion-exchange purification on Q-Sepharose column. FIG. 4D demonstrates binding of refolded B2M-aTac(dsFv)/G9-209M to the target antigen, p55. Detection of binding was with the conformational-specific MAb w6/32.

FIG. 2E demonstrates the nucleic (SEQ ID NO:4, linker sequence is shown in non-capital letters) and amino (SEQ ID NO:5) acid sequences of the B2M-aTacVL schematically illustrated in FIG. 2A as a part of B2M-aTac(dsFv).

FIG. 2F demonstrates the nucleic (SEQ ID NO:6) and amino (SEQ ID NO:7) acid sequences of the aTacVH schematically illustrated in FIG. 2A as a part of B2M-aTac(dsFv).

Figure 3A:
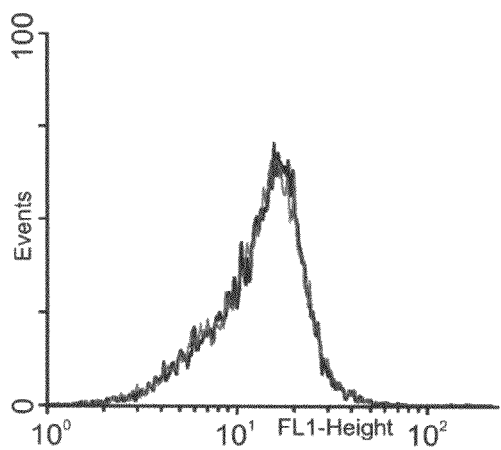
Figure 3B:
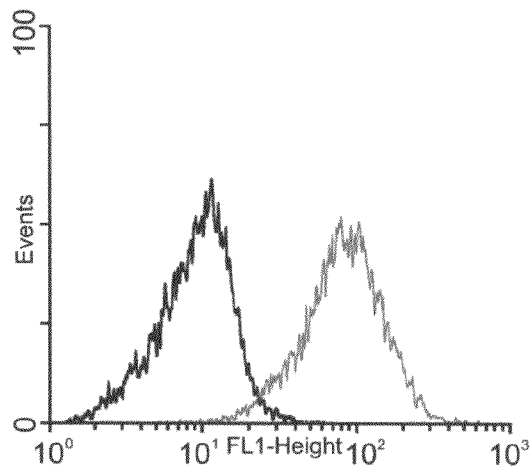
Figure 3C:
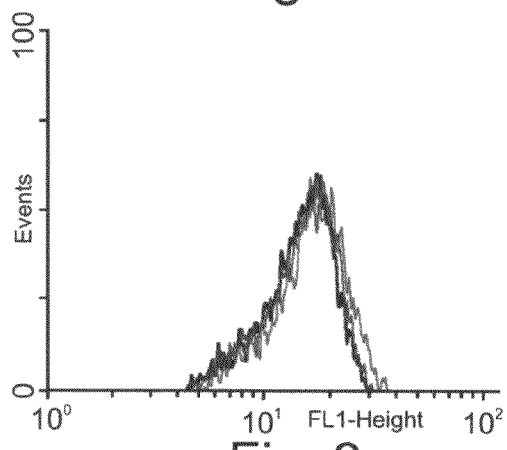
Figure 3D:
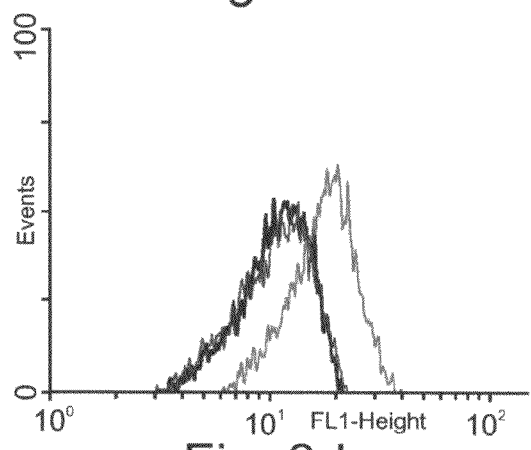
Figure 3E:
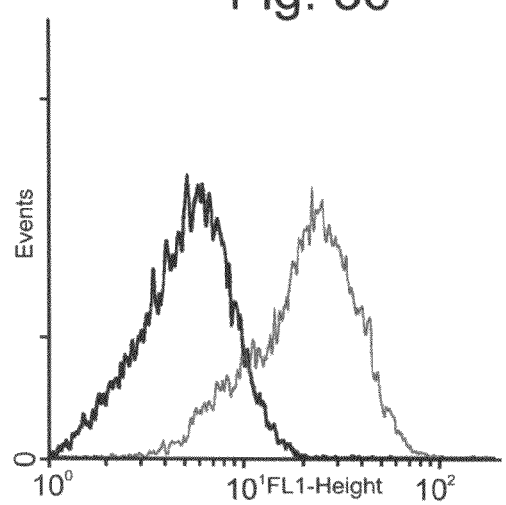
Figure 3F:
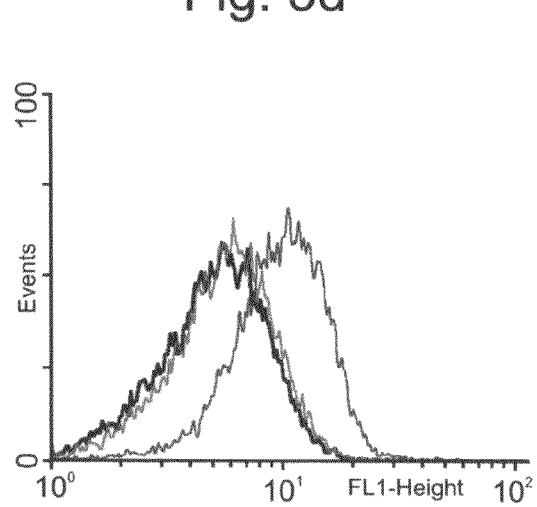

FIGS. 3A-F demonstrate binding of B2M-aTac(dsFv) to HLA-A2-negative tumor target cells. Flow cytometry analysis of the binding of B2M-aTac(dsFv) to antigen-positive HLA-A2-negative cells. FIG. 3A show binding of anti-Tac Mab (red) to A431; FIG. 3B shows binding of anti-Tac MAb to Tac (p55)-transfected A431 (ATAC4) cells (red); FIG. 3C shows binding of anti-HLA-A2 MAb BB7.2 to A431 cells incubated (red) or not (blue) with B2M-aTac(dsFv); FIG. 3D shows binding of MAb BB7.2 to p55-transfected ATAC4 cells preincubated (red) or not (blue) with B2M-aTac(dsFv); FIG. 3E shows binding of anti-Tac MAb (red) to leukemic HUT102W cells; and FIG. 3F shows binding of MAb BB7.2 to HUT102W cells preincubated (red) or not (blue) with B2M-aTac(dsFv). In all cases, control cells with secondary antibody are shown in black.

Figure 4A:
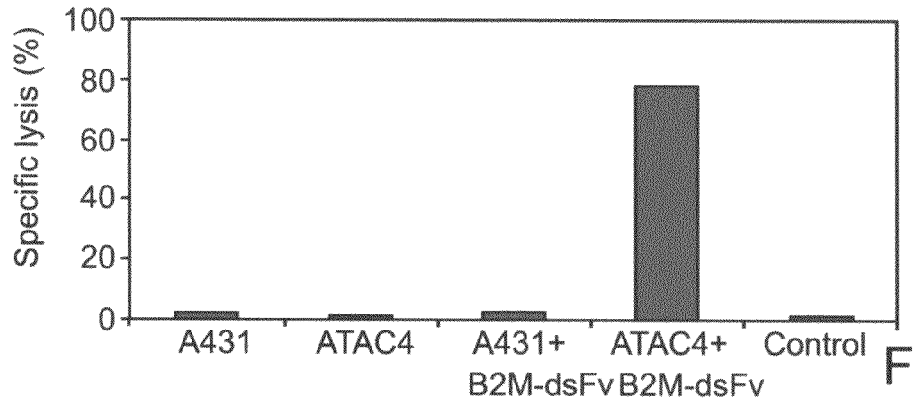
Figure 4B:
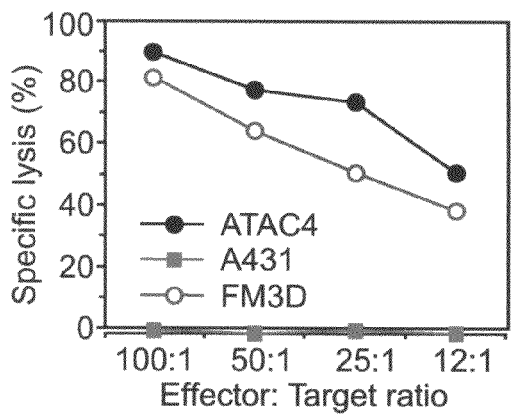
Figure 4C:
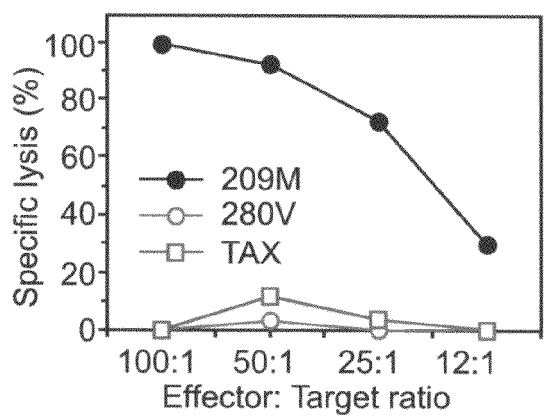
Figure 4D:
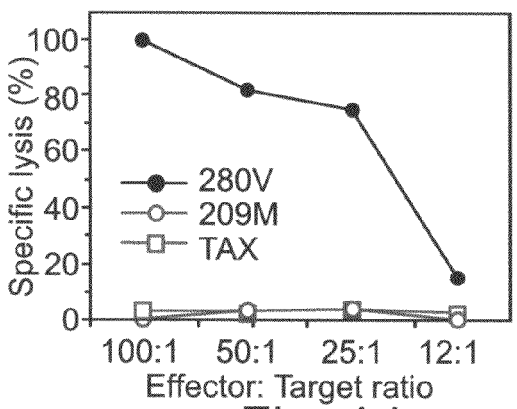
Figure 4E:
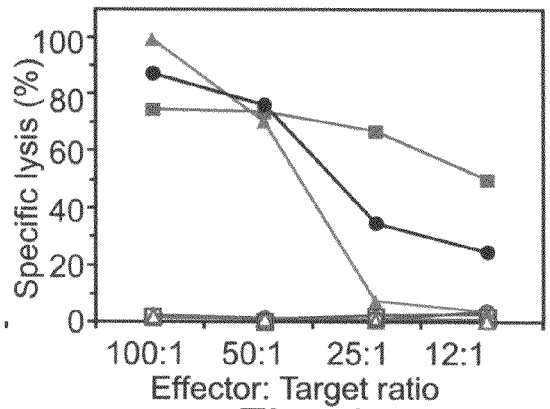

FIGS. 4A-E demonstrate potentiation of CTL-mediated lysis of HLA-A2-negative tumor cells by B2M-aTac(dsFv). Target cells coated or not with the B2M-aTac(dsFv)-peptide complexes were incubated with melanoma reactive gp100-peptide specific CTLs in a $^{35}$-Methionine-release assay. FIG. 4A—A431 and p55-transfected ATAC4 HLA-A2⁻ cells were preincubated or not with B2M-aTac(dsFv)/G9-209M complexes followed by incubation with the G9-209M-specific CTL, R6C12. Control are cells incubated with medium alone; FIG. 4B—A431 and p55-transfected ATAC4 HLA-A2⁻ cells were preincubated with B2M-aTac(dsFv)/G9-209M complexes followed by incubation with R6C12 CTLs. FM3D are HLA-A2⁺, gp100⁺ melanoma cells; FIGS. 4C and 4D—p55-transfected ATAC4 cells were preincubated with B2M-aTac (dsFv) complexes refolded with the HLA-A2-restricted peptides G9-209M, G9-280V, and TAX followed by incubation with the G9-209M-specific CTL clone R6C12 in FIG. 4C or the G9-280V-specific CTL clone R1E2 in FIG. 4D; FIG. 4E—HUT102W and CRII-2 HLA-A2⁻ leukemic cells were preincubated (w) or not (w/o) with B2M-aTac(dsFv) complexes containing the appropriate peptide followed by incubation with the G9-209M-specific R6C12 CTLs or G9-280V-specific R1E2 CTLs as indicated.

Figure 5:
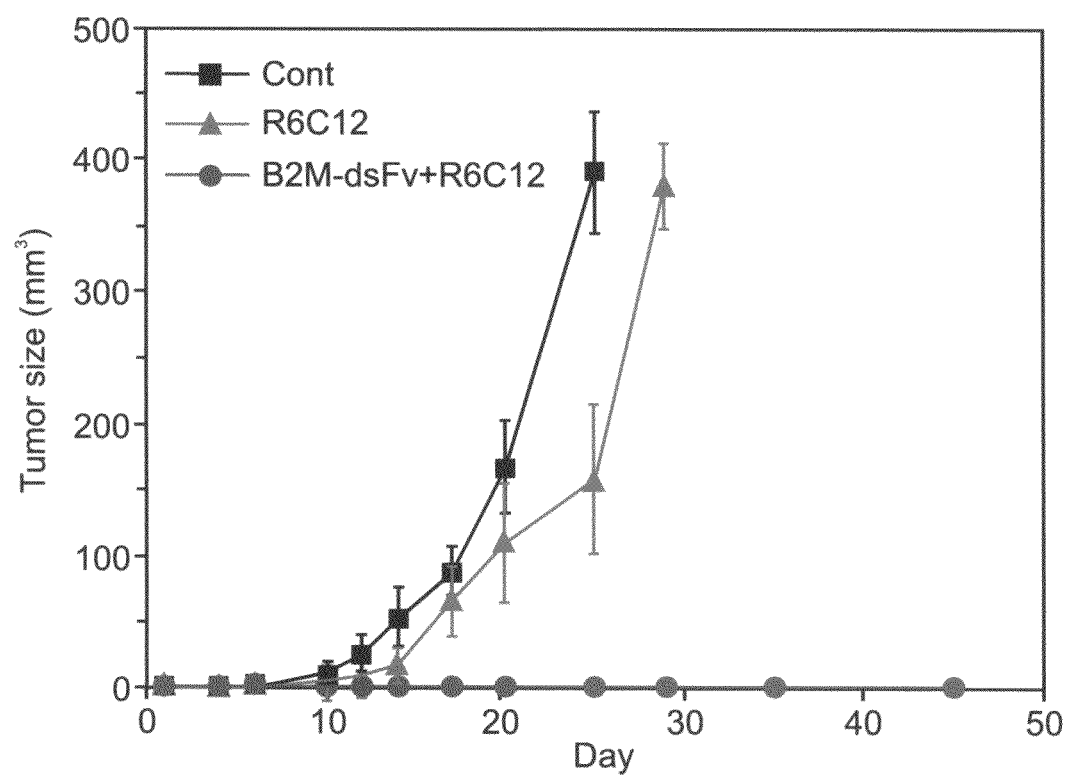

FIG. 5 is a plot demonstrating the results of an in vivo win assay with B2m-aTac(dsFv). ATAC4 cells ($1\times10^5$) were mixed with R6C12 CTL ($1\times10^6$) (E:T 10:1) in the presence or absence of B2M-aTac(dsFv) (20-50 g/ml) in 200 l. The mixture was injected subcotaneously to nude mice and the appearance of tumors was observed. ATAC4 cells alone were used as control.

Figure 6:
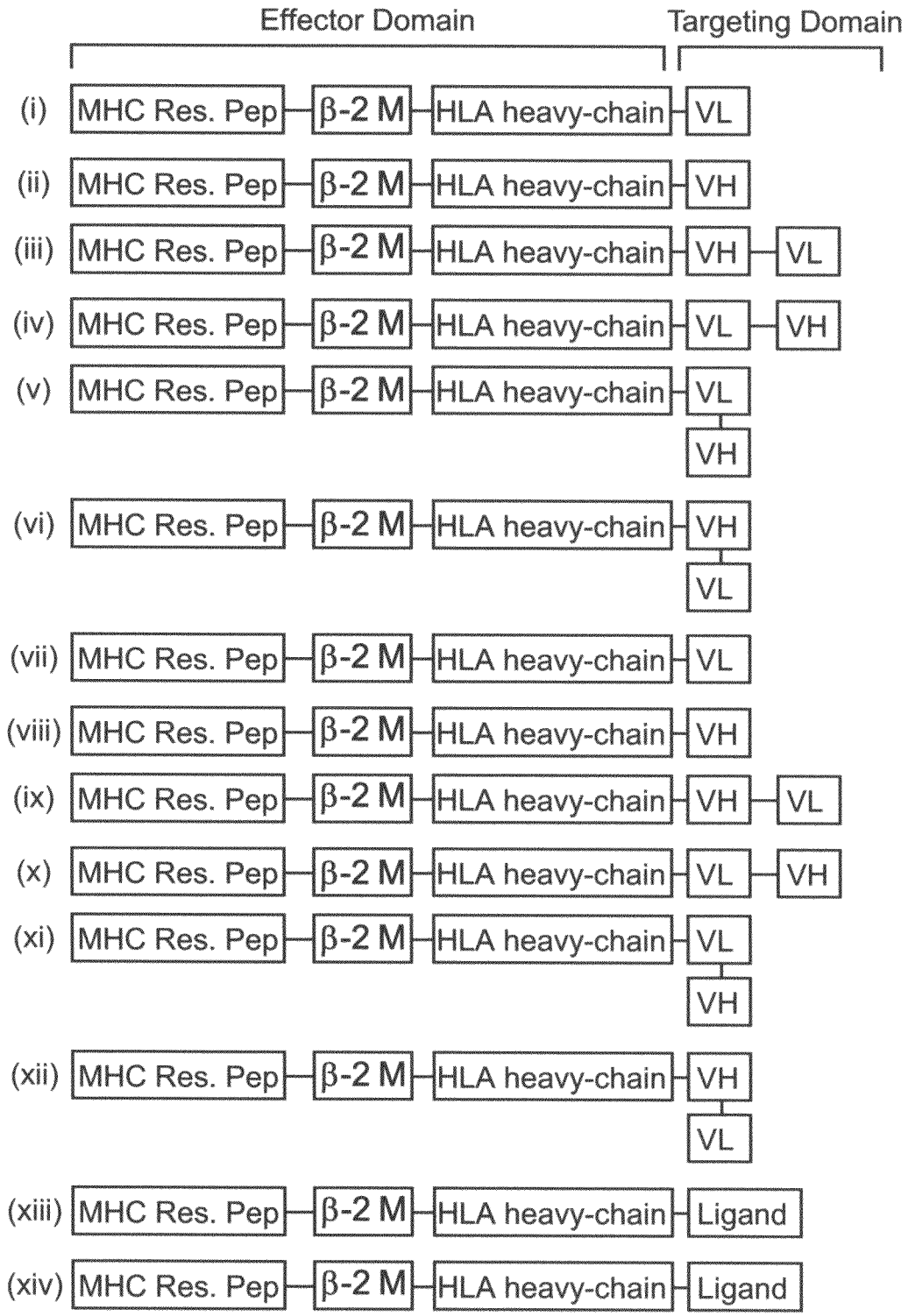

FIG. 6 is a schematic illustration of preferred immuno-molecules according to the present invention, wherein lines between boxes represent covalent linkage (e.g., translational fusion) between moieties in the boxes.

DESCRIPTION OF THE PREFERRED EMBODIMENTS

The present invention is of (i) novel immuno molecules; (ii) methods of preparing same; (iii) nucleic acid constructs encoding same; and (iv) methods of using same for selective killing of cells, cancer cells in particular.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Tumor progression is often associated with secretion of immune suppressive factors and/or downregulation of MHC class I antigen presentation functions (1-5, 14, 15). The inference is that tumors have elaborated strategies to circumvent an apparently effective immune response. Significant progress toward developing vaccines that can stimulate an immune response against tumors has involved the identification of the protein antigens associated with a given tumor type and epitope mapping of tumor antigens for HLA class I and class II restricted binding motifs were identified and are currently being used in various vaccination programs (6, 9, 11-13). MHC class I molecules presenting the appropriate peptides are necessary to provide the specific signals for recognition and killing by CTLs. However, the principle mechanism of tumor escape is the loss, downregulation or alteration of HLA profiles that may render the target cell unresponsive to CTL lysis, even if the cell expresses the appropriate tumor antigen. In human tumors, HLA loss may be as high as 50%, suggesting that a reduction in protein levels might offer a survival advantage to the tumor cells (14, 15).

The present invention presents a new approach to circumvent this problem. While reducing the present invention to practice, tumor-specific targeting of class I MHC-peptide complexes onto tumor cells was shown to be an effective and efficient strategy to render HLA-A2-negative cells susceptible to lysis by relevant HLA-A2-restricted CTLs. This new strategy of redirecting CTLs against tumor cells takes advantage of the use of recombinant antibody fragments or ligands that can localize on malignant cells that express a tumor marker (antigen, e.g., receptor), usually associated with the transformed phenotype (such as growth factor receptors, differentiation antigens), with a relatively high degree of specificity. The tumor targeting recombinant antibody fragments used while reducing the present invention to practice, constituted of the Fv variable domains which are the smallest functional modules of antibodies necessary to maintain antigen binding. This makes them especially useful for clinical applications, not only for generating the molecule described herein but also for making other antibody fusion proteins, such as recombinant Fv immunotoxins or recombinant antibody-cytokine fusions (37, 38), because their small size improves tumor penetration.

The antibody targeting fragment or targeting ligand is fused to a single-chain HLA molecule that can be folded efficiently and functionally around an HLA-A2-restricted peptide. This approach can be expanded to other major HLA alleles and many types of tumor specificities which are dictated by the recombinant antibody fragments, thus, generating a new family of immunotherapeutic agents that may be used to augment and potentiate anti-tumor activities. Together with the application of monoclonal antibodies for cancer therapy this approach may be regarded as a link between anti-tumor antibodies and cell-mediated immunotherapy.

Recombinant antibodies have been used already to redirect T cells using a classical approach of bispecific antibodies in which one antibody arm is directed against a tumor-specific antigen and the other arm against an effector cell-associated molecule such as CD3 for CTLs and CD16 for NK cells (39).

Ligands that bind to tumor cells have also been used already to target a variety of toxins to tumor cells. See, for example, references 50-52 with respect to EGF, TGF, IL-2 and IL-3.

A major advantage of the approach of the present invention is the use of a recombinant molecule that can be produced in a homogeneous form and large quantities. Importantly, the size of the B2M-dsFv molecule at approximately 65 kDa (generated with any antibody dsFv fragment) is optimal with respect to the requirements needed for good tumor penetration on one hand and relatively long half life and stability in the circulation of the other (40). A recent study describing the generation of antibody-class I MHC tetramers was published in which efficient CTL-mediated killing of tumor target cells was observed using Fab-streptavidin-MHC tetramer conjugates (41). The limitation of this approach, in comparison to the recombinant antibody fragment-monomeric scMHC fusion described herein, is the large size of these molecules of around 400 kDa and the fact that soluble MHC tetramers can induce T cell activation themselves whereas monomeric MHC molecule can not induce activation unless in a relatively high local concentration (42-44).

The coating of tumor cells which had downregulated their own MHC expression through the use of this targeting approach potentiates the cells for CTL-mediated killing while using a target on the tumor cells that is usually involved in the transformation process, most classical examples are growth factor receptors such as the IL-2R as used herein. This fact also favors the idea that using this approach escape mutants which down regulate the targeted receptor are not likely to have a growth advantage because the receptor is directly involved in key survival functions of the cancer cells.

Another advantage to the antibody approach presented herein is the fact that these new agents can be designed around the desired peptide specificity, namely the refolding of the B2M-Fv molecule can be performed around any appropriate MHC-restricted peptide. In the Examples presented herein, HLA-A2-restricted tumor-specific CTLs recognizing T cell epitopes derived from the melanoma differentiation antigen gp100 was employed. However, the kind of antigen-reactive CTL to be redirected to kill the tumor cells can be defined by other antigenic peptides based on recent knowledge of immune mechanisms in health and disease. For example, the identification of tumor-specific CTL responses in patients may suggest that these may be efficient to target. However, recent studies have demonstrated that these tumor-specific CTLs are not always optimal since they are often present only at very low frequencies or even when they are present at high frequencies they may be not functional or anergic (7). Thus, a more active and promising source of CTLs can be recruited from circulating lymphocytes directed against common and very immunogenic T cell epitopes such as derived from viruses or bacterial toxins which can also elicit a good memory response (45,46). It has been shown that CTL precursors directed against influenza, EBV, CMV epitopes (peptides) are maintained in high frequencies in the circulation of cancer patients as well as healthy individuals and these CTLs are usually active and with a memory phenotype (45, 46). Thus, these CTLs would be the source of choice to be redirected to the tumor cells through the use of a B2M-Fv molecule generated loaded with such viral-derived epitopes. The optimal agent is a B2M-Fv molecule in which the antigenic peptide is also covalently linked to the complex through the use of a flexible linker connecting the peptide to the N-terminus of the β-2 microglobulin. This construct will ensure optimal stability for the scMHC complex in vivo because the stabilizing peptide is connected covalently and can not leave easily the MHC peptide-binding groove. This type of single-chain peptide-MHC molecules were generated previously in murine and human systems for various functional and structural studies (47, 48). An additional option is to use antigenic peptide-derivatives that are modified at the "anchoring residues" in a way that increases their affinity to the HLA binding groove (27).

There are also several options for the type of Fv fragment to be used as the targeting moiety. In addition to the dsFv type of fragment, employed while reducing the present invention to practice, a single-chain Fv fragment (scFv) can be used in which the antibody VH and VL domains are connected via a peptide linker. In such case the B2M-Fv molecule is encoded by one plasmid which avoids possible contamination with single-domain B2M molecules.

Another important aspect of the present invention which is supported by others is the fact that the coating of antigenic MHC-peptide complexes on the surface of tumor cells without transmembrane anchoring is sufficient to induce their efficient lysis by specific CTLs without the knowledge whether autologous accessory molecules of the target tumor cells are present at all and are playing a role in such CTL-mediated killing. This observation results from the fact that a local high concentration of coated MHC-peptide complexes displaying one particular T cell epitope (peptide) is formed on the targeted cells which greatly exceeds the natural density of such complexes displayed on the surface of cells. In the case of the IL-2R α subunit, several hundred to thousands sites per cell are present on the target cells, in comparison to very few complexes containing one particular peptide expected to be present on cells, which may be sufficient for effective and efficient killing even without the involvement of accessory molecules. This is without taking into consideration the downregulation of class I MHC expression as an escape mechanism. Further indication for this possibility is found through the findings that MHC tetramers can induce T cell activation by themselves (44) including the recent observation that CTL activation by MHC tetramers without accessory molecules can be demonstrated at the single cell level (Cohen, Denkberg, Reiter; manuscript submitted).

In conclusion, the results presented herein provide a clear demonstration of the usefulness of the approach of the present invention to recruit active CTLs for tumor cell killing via cancer-specific antibody or ligand guided targeting of scMHC-peptide complexes. These results pave the way for the development of a new immunotherapeutic approach based on naturally occurring cellular immune responses which are redirected against the tumor cells.

According to one aspect of the present invention there is provided an immuno-molecule which comprises a soluble human MHC class I effector domain; and a targeting domain, either antibody targeting domain or ligand targeting domain, which is linked to the soluble human MHC class I effector domain. Preferably, the immuno-molecule has a molecular weight below 100 kDa. The soluble human MHC class I effector domain and the targeting domain are preferably translationally fused, optionally with a translationally fused peptide linker in-between. However, other ways to covalently link the soluble human MHC class I effector domain and the targeting domain are described hereinbelow.

FIG. 6 demonstrates several preferred immuno-molecules of the present invention, identified as (i)-(xiv). All of the molecules comprise a single chain and soluble MHC, which includes functional human β-2 microglobulin linked to functional human MHC class I heavy chain, which preferably comprises domains a 1-3. Preferably, the functional human β-2 microglobulin and the functional human MHC class I heavy chain are translationally fused, optionally with a translationally fused peptide linker in-between. However, as if further detailed below, the functional human β-2 microglobulin and the functional human MHC class I heavy chain can be covalently linked to one another in other ways.

As used herein the term "functional" when used in reference to the β-2 microglobulin and heavy chain polypeptides of a single chain MHC class I complex refers to any portion of each which is capable of contributing to the assembly of a functional single chain MHC class I complex (i.e., capable of binding and presenting to CTLs specific MHC-restricted antigenic peptides when complexed).

The phrases "translationally fused" and "in frame" are interchangeably used herein to refer to polypeptides encoded by polynucleotides which are covalently linked to form a single continuous open reading frame spanning the length of the coding sequences of the linked polynucleotides. Such polynucleotides can be covalently linked directly or preferably indirectly through a spacer or linker region encoding a linker peptide.

Molecules (i)-(vi) and (xiii) further comprise a MHC-restricted peptide covalently linked thereto. The MHC-restricted peptide is preferably linked to the functional human β-2 microglobulin. Preferably, the MHC-restricted peptide and the functional human β-2 microglobulin are translationally fused, optionally with a translationally fused peptide linker in-between. However, as if further detailed below, the MHC-restricted peptide and the functional human β-2 microglobulin can be covalently linked to one another in other ways.

Molecules (vii)-(xii) and (xiv) further comprise a MHC-restricted peptide which is not covalently linked thereto. In both cases, however, the MHC-restricted peptide is selected to complex with the functional human MHC class I heavy chain upon refolding, as if further described below.

The MHC-restricted peptide is preferably derived from a common pathogen, such as influenza, hepatitis, etc. The pathogen from which the MHC-restricted peptide is derived is selected according to several criteria as follows: (i) preferably, a large portion of the population was exposed to the pathogen or its antigens via infection of vaccination; (ii) an active vaccination is available for the pathogen, so as to be able to boost the immune response; and (iii) relatively high titer of CTLs with long term memory for the pathogen are retained in infected or vaccinated patients.

In the alternative, the MHC peptide is derived from a tumor associated or specific antigen. It was shown that MHC-restricted peptides derived from tumor associated or specific antigen can be used to elicit an efficient CTL response. To this end, see, for example, WO 00/06723, which is incorporated herein by reference.

The targeting domain can be an antibody targeting domain (molecules (i)-(xii)) or a ligand targeting domain (molecules (xiii) and (xiv)).

According to a one preferred embodiment of the present invention the antibody targeting domain comprises a variable region of a light chain of an antibody linked to the effector domain (see molecules (i) and (vii) of FIG. 6). Preferably, the variable region of the light chain of the antibody and the effector domain are translationally fused, optionally with a translationally fused peptide linker in-between. However, other ways to covalently link the variable region of the light chain of the antibody and the effector domain are described below.

According to another preferred embodiment, the antibody targeting domain further comprises a variable region of a heavy chain of an antibody linked to the variable region of the light chain of the antibody (see molecules (iii)-(vi) and (ix)-(xii) of FIG. 6). Preferably, the variable region of the heavy chain of the antibody and the variable region of the light chain of the antibody are translationally fused, optionally with a translationally fused peptide linker in-between (see molecules (vi) and (x) of FIG. 6). However, other ways to covalently link the variable region of the heavy chain of the antibody and the variable region of the light chain of the antibody are disclosed herein.

For example, the variable region of the heavy chain of the antibody can be linked to the variable region of the light chain of the antibody via at least one S—S bond, generating a dsFV moiety (see, for example, molecules (v) and (xi) in FIG. 6)).

According to a another preferred embodiment of the present invention the antibody targeting domain comprises a variable region of a heavy chain of an antibody linked to the effector domain (see molecules (ii) and (viii) of FIG. 6). Preferably, the variable region of the heavy chain of the antibody and the effector domain are translationally fused, optionally with a translationally fused peptide linker in-between (see molecules (iii) and (ix) of FIG. 6). However, other ways to covalently link the variable region of the heavy chain of the antibody and the effector domain are described below.

According to another preferred embodiment, the antibody targeting domain further comprises a variable region of a light chain of an antibody linked to the variable region of the heavy chain of the antibody (see molecules (iii), (vi), (ix) and (xii) of FIG. 6). Preferably, the variable region of the light chain of the antibody and the variable region of the heavy chain of the antibody are translationally fused, optionally with a translationally fused peptide linker in-between (see molecules (iii) and (ix) of FIG. 6). However, other ways to covalently link the variable region of the light chain of the antibody and the variable region of the heavy chain of the antibody are disclosed herein.

For example, the variable region of the light chain of the antibody can be linked to the variable region of the heavy chain of the antibody via at least one S—S bond, generating a dsFV moiety (see, for example, molecules (vi) and (xii) in FIG. 6)).

The antibody targeting domain in the molecule of the invention is selected capable of binding to a tumor associated or specific antigen. It will be appreciated in this respect that presently there are several hundred identified tumor associated or specific antigens, associated with various solid and non solid tumors, and further that monoclonal antibodies were developed for many of which. In other words, the amino acid and nucleic acid sequences of many antibodies which specifically bind to tumor associated or specific antigens is either already known or can be readily determined by analyzing the hybridomas producing such antibodies.

The molecules described in FIG. 6 are composed of a single polypeptide [e.g., molecules (i)-(iv) and (xiii)], two polypeptides [molecules (v), (vi), (vi)-(x) and (xiv)] or three polypeptides [molecules (xi) and (xii)].

The terms peptide and polypeptide are used herein interchangeably. Each of the polypeptides can be synthesized using any method known in the art. Hence, it will be appreciated that the immuno-molecules of the present invention or portions thereof can be prepared by several ways, including solid phase protein synthesis, however, in the preferred embodiment of the invention, at least major portions of the molecules, e.g., the soluble human MHC class I effector domain (with or without the MHC-restricted peptide) and the antibody targeting domain (as a scFV or as an arm of a dsFv) are generated by translation of a respective nucleic acid construct or constructs.

So, one to three open reading frames are required to synthesize the molecules of FIG. 6 via translation. These open reading frames can reside on a single, two or three nucleic acid molecules. Thus, for example, a single nucleic acid construct can carry all one, two or three open reading frames. One to three cis acting regulatory sequences can be used to control the expression of the one to three open reading frames. For example, a single cis acting regulatory sequence can control the expression of one, two or three open reading frames, in a cistrone-like manner. In the alternative, three independent cis acting regulatory sequences can be used to control the expression of the three open reading frames. Other combinations are also envisaged.

In cases where the MHC-restricted peptide is not covalently linked to the remaining portions of the molecule (see in FIG. 6 molecules (vii)-(xii)), it is preferably prepared via solid phase techniques, as it is generally a short peptide of less than 10 amino acids.

The open reading frames and the cis acting regulatory sequences can be carried by one to three nucleic acid molecules. For example, each open reading frame and its cis acting regulatory sequence are carried by a different nucleic acid molecule, or all of the open reading frames and their associated cis acting regulatory sequences are carried by a single nucleic acid molecule. Other combinations are also envisaged.

Expression of the polypeptide(s) can be effected by transformation/transfection and/or co-transformation/co-transfection of a single cell or a plurality of cells with any of the nucleic acid molecules, serving as transformation/transfection vectors (e.g., as plasmids, phages, phagemids or viruses).

Hence, according to another aspect of the present invention there is provided a nucleic acid construct encoding an immuno-molecule. The construct according to this aspect of the invention comprises a first polynucleotide encoding a soluble human MHC class I effector domain; and a second polynucleotide encoding a targeting domain, either an antibody targeting domain or a ligand targeting domain. The first polynucleotide and the second polynucleotide are selected and being joined together such that the soluble human MHC class I effector domain and the targeting domain are translationally fused, optionally via a peptide linker in-between.

According to still another aspect of the present invention there is provided a nucleic acid construct encoding an immuno-molecule. The construct according to this aspect of the invention comprises a first polynucleotide encoding a soluble human MHC class I effector domain; and a second polynucleotide encoding a variable region of one of a light chain or a heavy chain of an antibody targeting domain. The first polynucleotide and the second polynucleotide are selected and being joined together such that the soluble human MHC class I effector domain and the variable region of the one of the light chain and heavy chain of the antibody targeting domain are translationally fused optionally via a peptide linker in-between. The construct according to this aspect of the invention further comprises and a third polynucleotide encoding the other of the one of the light chain and heavy chain of the antibody targeting domain. The third polynucleotide may be selected so as to encode a separate polypeptide, so as to allow generation of a dsFV, or to encode a polypeptide which is translationally fused to the second nucleic acid, so as to allow generation of a scFV.

According to an additional aspect of the present invention there is provided a nucleic acid construct system. The construct system comprises a first nucleic acid construct which comprises a first polynucleotide encoding a soluble human MHC class I effector domain; and a second polynucleotide encoding a variable region of one of a light chain or a heavy chain of an antibody targeting domain. The first polynucleotide and the second polynucleotide are selected and being joined together such that the soluble human MHC class I effector domain and the variable region of the one of the light chain and heavy chain of the antibody targeting domain are translationally fused optionally via a peptide linker in-between. The construct system further comprises a second nucleic acid construct which comprises a third polynucleotide encoding the other of the one of the light chain and heavy chain of the antibody targeting domain. These constructs may be cointroduced into the same cell or into different cells. In the first case, the constructs making the construct system may be mixed together, whereas in the second case, the constructs making the construct system are kept unmixed in separate containers.

Whenever and wherever used, the linker peptide is selected of an amino acid sequence which is inherently flexible, such that the polypeptides connected thereby independently and natively fold following expression thereof, thus facilitating the formation of a functional single chain (sc) human MHC class I complex, targeting scFv or ligand and/or human MHC class I-MHC restricted antigen complex.

Any of the nucleic acid constructs described herein comprise at least one cis acting regulatory sequence operably linked to the coding polynucleotides therein. Preferably, the cis acting regulatory sequence is functional in bacteria. Alternatively, the cis acting regulatory sequence is functional in yeast. Still alternatively, the cis acting regulatory sequence is functional in animal cells. Yet alternatively, the cis acting regulatory sequence is functional in plant cells.

The cis acting regulatory sequence can include a promoter sequence and additional transcriptional or a translational enhancer sequences all of which serve for facilitating the expression of the polynucleotides when introduced into a host cell. Specific examples of promoters are described hereinbelow in context of various eukaryotic and prokaryotic expression systems and in the Examples section which follows.

It will be appreciated that a single cis acting regulatory sequence can be utilized in a nucleic acid construct to direct transcription of a single transcript which includes one or more open reading frames. In the later case, an internal ribosome entry site (IRES) can be utilized so as to allow translation of the internally positioned nucleic acid sequence.

According to another aspect of the present invention there is provided a transformed cell which comprises any one or more of the nucleic acid constructs or the nucleic acid construct system described herein. The cell, according to this aspect of the invention can be a eukaryotic cell selected from the group consisting of a mammalian cell, an insect cell, a plant cell, a yeast cell and a protozoa cell, or it can be a bacterial cell.

Whenever co-expression of independent polypeptides in a single cell is of choice, the construct or constructs employed must be configured such that the levels of expression of the independent polypeptides are optimized, so as to obtain highest proportions of the final product.

Preferably a promoter (being an example of a cis acting regulatory sequence) utilized by the nucleic acid construct(s) of the present invention is a strong constitutive promoter such that high levels of expression are attained for the polynucleotides following host cell transformation.

It will be appreciated that high levels of expression can also be effected by transforming the host cell with a high copy number of the nucleic acid construct(s), or by utilizing cis acting sequences which stabilize the resultant transcript and as such decrease the degradation or "turn-over" of such a transcript.

As used herein, the phrase "transformed cell" describes a cell into which an exogenous nucleic acid sequence is introduced to thereby stably or transiently genetically alter the host cell. It may occur under natural or artificial conditions using various methods well known in the art some of which are described in detail hereinbelow in context with specific examples of host cells.

The transformed host cell can be a eukaryotic cell, such as, for example, a mammalian cell, an insect cell, a plant cell, a yeast cell and a protozoa cell, or alternatively, the cell can be a bacterial cell.

When utilized for eukaryotic host cell expression, the nucleic acid construct(s) according to the present invention can be a shuttle vector, which can propagate both in *E. coli* (wherein the construct comprises an appropriate selectable marker and origin of replication) and be compatible for expression in eukaryotic host cells. The nucleic acid construct(s) according to the present invention can be, for example, a plasmid, a bacmid, a phagemid, a cosmid, a phage, a virus or an artificial chromosome.

According to another preferred embodiment of the present invention the host cell is a mammalian cell of, for example, a mammalian cell culture. Suitable mammalian expression systems include, but are not limited to, pcDNA3, pcDNA3.1 (+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

Insect cell cultures can also be utilized to express the nucleic acid sequences of the present invention. Suitable insect expression systems include, but are not limited to the baculovirus expression system and its derivatives which are commercially available from numerous suppliers such as Invitrogen (maxBac™) Clontech (BacPak™), or Gibco (Bac-to-Bac™).

Expression of the nucleic acid sequences of the present invention can also be effected in plants cells. As used herein, the phrase "plant cell" can refer to plant protoplasts, cells of a plant tissue culture, cells of plant derived tissues or cells of whole plants.

There are various methods of introducing nucleic acid constructs into plant cells. Such methods rely on either stable integration of the nucleic acid construct or a portion thereof into the genome of the plant cell, or on transient expression of the nucleic acid construct in which case these sequences are not stably integrated into the genome of the plant cell.

There are two principle methods of effecting stable genomic integration of exogenous nucleic acid sequences such as those included within the nucleic acid construct of the present invention into plant cell genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure, see for example, Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of stably transformed dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues. Direct DNA transfer can also be utilized to transiently transform plant cells.

In any case suitable plant promoters which can be utilized for plant cell expression of the first and second nucleic acid sequences, include, but are not limited to CaMV 35S promoter, ubiquitin promoter, and other strong promoters which can express the nucleic acid sequences in a constitutive or tissue specific manner.

Plant viruses can also be used as transformation vectors. Viruses that have been shown to be useful for the transformation of plant cell hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the nucleic acid sequences described above. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

Yeast cells can also be utilized as host cells by the present invention. Numerous examples of yeast expression vectors suitable for expression of the nucleic acid sequences of the present invention in yeast are known in the art and are commercially available. Such vectors are usually introduced in a yeast host cell via chemical or electroporation transformation methods well known in the art. Commercially available systems include, for example, the pYES™ (Invitrogen) or the YEX™ (Clontech) expression systems.

It will be appreciated that when expressed in eukaryotic expression systems such as those described above, the nucleic acid construct preferably includes a signal peptide encoding sequence such that the polypeptides produced from the first and second nucleic acid sequences are directed via the attached signal peptide into secretion pathways. For example, in mammalian, insect and yeast host cells, the expressed polypeptides can be secreted to the growth medium, while in plant expression systems the polypeptides can be secreted into the apoplast, or directed into a subcellular organelle.

According to a presently most preferred embodiment of the invention, the host cell is a bacterial cell, such as, for example, *E. coli*. A bacterial host can be transformed with the nucleic acid sequence via transformation methods well known in the art, including for example, chemical transformation (e.g., $CaCl_2$) or electroporation.

Numerous examples of bacterial expression systems which can be utilized to express the nucleic acid sequences of the present invention are known in the art. Commercially available bacterial expression systems include, but are not limited to, the pET™ expression system (Novagen), pSE™ expression system (Invitrogen) or the pGEX™ expression system (Amersham).

As is further described in the Examples section which follows, bacterial expression is particularly advantageous since the expressed polypeptides form substantially pure inclusion bodies readily amenable to recovery and purification of the expressed polypeptide.

Thus, according to yet another aspect of the present invention there is provided a preparation of bacterial derived inclusion bodies which are composed of over 30 percent, preferably over 50%, more preferably over 75%, most preferably over 90% by weight of the recombinant polypeptide or a mixture of polypeptides of the present invention. The isolation of such inclusion bodies and the purification of the polypeptide(s) therefrom are described in detail in the Examples section which follows.

As demonstrated in the Examples section that follows, bacterial expression of the polypeptide(s) can provide high quantities of pure and functional immunomolecules.

According to an additional aspect of the present invention there is provided a method of producing an immunomolecule of the invention. The method according to this aspect of the present invention utilizes any of the nucleic acid construct(s) described for expressing, in bacteria, a the polypeptide(s) described herein.

Following expression, the polypeptide(s) is/are isolated and purified as described below.

As is further described in the Examples section which follows, the expressed polypeptide(s) form substantially pure inclusion bodies which are readily isolated via fractionation techniques well known in the art and purified via for example denaturing-renaturing steps.

Preferably, the polypeptide(s) of the invention are renatured and refolded in the presence of a MHC-restricted peptide, which is either linked to, co-expressed with or mixed with other polypeptides of the invention and being capable of binding the single chain MHC class I polypeptide. As is further described in the Examples section this enables to generate a substantially pure MHC class I-antigenic peptide complex which can further be purified via size exclusion chromatography.

It will be appreciated that the MHC-restricted peptide used for refolding can be co-expressed along with (as an independent peptide) or be fused to the soluble human MHC class I polypeptide in the bacteria. In such a case the expressed polypeptide and peptide co-form inclusion bodies which can be isolated and utilized for MHC class I-antigenic peptide complex formation.

According to a further aspect of the present invention there is provided a method of selectively killing a cell in a patient, the cell presenting an antigen (e.g., a receptor). The method according to this aspect of the invention comprises administering to the patient an immuno-molecule which comprises: a soluble human MHC class I effector domain complexed with an MHC-restricted peptide; and a targeting domain, either antibody or ligand targeting domain, being linked to the soluble human MHC class I effector domain. The targeting domain serves for selectively binding to the antigen; whereby, the soluble human MHC class I effector domain complexed with the MHC-restricted peptide initiates a CTL mediated immune response against the cell, thereby selectively killing the cell in vivo. The cell to be killed can be a cancer cell, in which case, the targeting domain will be selected binding to a tumor associated antigen characterized for said cancer cell.

The following sections provide specific examples and alternatives for each of the various aspects of the invention described herein. These examples and alternatives should not be regarded as limiting in any way, as the invention can be practiced in similar, yet somewhat different ways. These examples, however, teach one of ordinary skills in the art how to practice various alternatives and embodiments of the invention.

Antibody:

The term "antibody" and the phrase "antibody targeting domain" as used to describe this invention includes intact molecules as well as functional fragments thereof, such as Fab, F(ab')$_2$, Fv and scFv that are capable of specific, high affinity binding to an antigen. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (c) scFv or "single chain antibody" ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

The humanized antibody optimally also will comprise at least a portion of an immunoglobulin constant region (Fc), typically that of a human immunoglobulin [Jones et al., Nature, 321:522-525 (1986); Riechmann et al., Nature, 332: 323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

It will be appreciated that once the CDRs of an antibody are identified, using conventional genetic engineering techniques can be used to devise expressible polynucleotides encoding any of the forms or fragments of antibodies described herein.

Ligand

The Table below provides non exhaustive examples of receptors selectively expressed by a variety of tumor cells, their ligands and sequence information pertaining to the ligands, which sequence information can be used in the construction of constructs and immuno-molecules according to the present invention:

| Receptor | Tumor (Ref) | Ligand | Genebank Accession No. (Nucleic acid sequence) | Genebank Accession No. (Amino acid Sequence) |
|---|---|---|---|---|
| EGFR | Breast, Brain, Lung (Niv et al Curr. Pharm. Biotech. 2: 19-46, 2002) | EGF | L17029 | AAB32226 |
| PDGFR | Ovary, Breast | PDGF | XO6374 | CAA29677 |
| Mutant EGFR | Liver, Brain | EGF | S51343 | AAB19486 |
| IL-4R | Renal | IL-4 | M13982 | AAA59149 |
| IL-6R | Myeloma | IL-6 | M14584 | AAA59149 |
| IL-10R | Leukemias | IL-10 | M57627 | AAA63207 |
| EGFR | Breast, Ovary, | TGF | M31172 | AAA61157 |
| VEGFR | Carcinomas blood vessels | VEGF | M32977 | AAA35789 |
| KDR | Carcinomas blood vessels | VEGF | M32977 | AAA35789 |

A Human Major Histocompatibility Complex (MHC) Class I:

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

Major histocompatibility complex (MHC) class I molecules are expressed on the surface of nearly all cells. These molecules function in presenting peptides which are mainly derived from endogenously synthesized proteins to CD8+ T cells via an interaction with the $\alpha\beta$ T-cell receptor. The class I MHC molecule is a heterodimer composed of a 46-kDa heavy chain which is non-covalently associated with the 12-kDa light chain $\beta$-2 microglobulin. In humans, there are several MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, their sequences can be found at the kabat database of Sequences of Proteins of Immunological Interest which is incorporated herein by reference.

Peptides that Bind to Class I MHC Molecules; MHC-Restricted Antigens:

Class I, MHC-restricted peptides (also referred to herein interchangeably as MHC-restricted antigens, HLA-restricted peptides, HLA-restricted antigens) which are typically 8-10-amino acid-long, bind to the heavy chain $\alpha1$-$\alpha2$ groove via two or three anchor residues that interact with corresponding binding pockets in the MHC molecule. The $\beta$-2 microglobulin chain plays an important role in MHC class I intracellular transport, peptide binding, and conformational stability. For most class I molecules, the formation of a heterodimer consisting of the MHC class I heavy chain, peptide (self or antigenic) and β-2 microglobulin is required for biosynthetic maturation and cell-surface expression.

Research studies performed on peptide binding to class I MHC molecules enable to define specific MHC motifs functional in displaying peptides derived from viral, tumor and self antigens that are potentially immunogenic and might elicit specific response from cytotoxic T lymphocytes (CTLs).

As used herein the term "peptide" refers to native peptides (either degradation products or synthetically synthesized peptides) and further to peptidomimetics, such as peptoids and semipeptoids which are peptide analogs, which may have, for example, modifications rendering the peptides more stable while in a body, or more immunogenic. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C.A. Ramsden Gd., Chapter 17.2, F. Choplin Pergamon Press (1992), which is incorporated by reference as if fully set forth herein. Further detail in this respect are provided hereinunder.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids useful in MHC-1HLA-A2 recognizable peptide antigens are given hereinunder.

Based on accumulated experimental data, it is nowadays possible to predict which of the peptides of a protein will bind to MHC, class I. The HLA-A2 MHC class I has been so far characterized better than other HLA haplotypes, yet predictive and/or sporadic data is available for all other haplotypes.

With respect to HLA-A2 binding peptides, assume the following positions (P1-P9) in a 9-mer peptide:

P1-P2-P3-P4-P5-P6-P7-P8-P9

The P2 and P2 positions include the anchor residues which are the main residues participating in binding to MHC molecules. Amino acid resides engaging positions P2 and P9 are hydrophilic aliphatic non-charged natural amino (examples being Ala, Val, Leu, Ile, Gln, Thr, Ser, Cys, preferably Val and Leu) or of a non-natural hydrophilic aliphatic non-charged amino acid (examples being norleucine (Nle), norvaline (Nva), α-aminobutyric acid). Positions P1 and P3 are also known to include amino acid residues which participate or assist in binding to MHC molecules, however, these positions can include any amino acids, natural or non-natural. The other positions are engaged by amino acid residues which typically do not participate in binding, rather these amino acids are presented to the immune cells. Further details relating to the binding of peptides to MHC molecules can be found in Parker, K. C., Bednarek, M. A., Coligan, J. E., Scheme for ranking potential HLA-A2 binding peptides based on independent binding of individual peptide side-chains. J Immunol. 152, 163-175, 1994, see Table V, in particular. Hence, scoring of HLA-A2.1 binding peptides can be performed using the HLA Peptide Binding Predictions software. This software is based on accumulated data and scores every possible peptide in an analyzed protein for possible binding to MHC HLA-A2.1 according to the contribution of every amino acid in the peptide. Theoretical binding scores represent calculated half-life of the HLA-A2.1-peptide complex.

Hydrophilic aliphatic natural amino acids at P2 and P9 can be substituted by synthetic amino acids, preferably Nleu, Nval and/or α-aminobutyric acid. P9 can be also substituted by aliphatic amino acids of the general formula —HN($CH_2$)$_n$COOH, wherein n=3-5, as well as by branched derivatives thereof, such as, but not limited to,

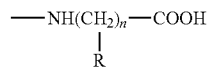

wherein R is, for example, methyl, ethyl or propyl, located at any one or more of the n carbons.

The amino terminal residue (position P1) can be substituted by positively charged aliphatic carboxylic acids, such as, but not limited to, $H_2N(CH_2)_n$COOH, wherein n=2-4 and $H_2N$—C(NH)—NH($CH_2$)$_n$COOH, wherein n=2-3, as well as by hydroxy Lysine, N-methyl Lysine or ornithine (Orn). Additionally, the amino terminal residue can be substituted by enlarged aromatic residues, such as, but not limited to, $H_2N$—($C_6H_6$)—$CH_2$—COOH, p-aminophenyl alanine, $H_2N$—F(NH)—NH—($C_6H_6$)—$CH_2$—COOH, p-guanidinophenyl alanine or pyridinoalanine (Pal). These latter residues may form hydrogen bonding with the OH⁻ moieties of the Tyrosine residues at the MHC-1 N-terminal binding pocket, as well as to create, at the same time aromatic-aromatic interactions.

Derivatization of amino acid residues at positions P4-P8, should these residues have a side-chain, such as, OH, SH or $NH_2$, like Ser, Tyr, Lys, Cys or Orn, can be by alkyl, aryl, alkanoyl or aroyl. In addition, OH groups at these positions may also be derivatized by phosphorylation and/or glycosylation. These derivatizations have been shown in some cases to enhance the binding to the T cell receptor.

Longer derivatives in which the second anchor amino acid is at position P10 may include at P9 most L amino acids. In some cases shorter derivatives are also applicable, in which the C terminal acid serves as the second anchor residue.

Cyclic amino acid derivatives can engage position P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)$_n$—COOH)—C(R)H—COOH or H—N(($CH_2$)$_n$—COOH)—C(R)H—$NH_2$, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom.

These modifications can occur at any of the bonds along the peptide chain and even at several (2-3) at the same time. Preferably, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Tumor MHC-Restricted Antigens:

The references recited in the following Table provide examples of human MHC class I, tumor MHC-restricted peptides derived from tumor associated antigens (TAA) or protein markers associated with various cancers. Additional tumor MHC-restricted peptides derived from tumor associated antigens (TAA) can be found on the BMI Biomedical Informatics Heidelberg website.

| Cancer | TAA/Marker | HLA | Reference |
|---|---|---|---|
| Transitional cell carcinoma | Uroplakin II | HLA-A2 | WO 00/06723 |
| Transitional cell carcinoma | Uroplakin Ia | HLA-A2 | WO 00/06723 |
| Carcinoma of the prostate | prostate specific antigen | HLA-A2 | WO 00/06723 |
| Carcinoma of the prostate | prostate specific membrane antigen | HLA-A2 | WO 00/06723 |
| Carcinoma of the prostate | prostate acid phosphatase | HLA-A2 | WO 00/06723 |
| Breast cancer | BA-46 | HLA-A2 | WO 00/06723 |
| Breast cancer | Muc-1 | HLA-A2 | WO 00/06723 |
| Melanoma | Gp100 | HLA-A2 | Reference 54 |
| Melanoma | MART1 | HLA-A2 | Reference 54 |
| All tumors | Telomerase | HLA-A2 | Reference 54 |
| Leukemia | TAX | HLA-A2 | Reference 54 |
| Carcinomas | NY-ESO | HLA-A2 | Reference 54 |
| Melanoma | MAGE-A1 | HLA-A2 | Reference 54 |
| Melanoma | MAGE-A3 | HLA-A24 | Reference 54 |
| Carcinomas | HER2 | HLA-A2 | Reference 54 |
| Melanoma | Beta-catenine | HLA-A24 | Reference 54 |
| Melanoma | Tyrosinase | HLA-DRB1 | Reference 54 |
| Leukemia | Bcr-abl | HLA-A2 | Reference 54 |
| Head and neck | Caspase 8 | HLA-B35 | Reference 54 |

Viral MHC-Restricted Antigens:

The references recited in the following Table provide examples of human MHC class I, viral MHC-restricted peptides derived from viral antigens.

| Disease | Viral antigen | HLA |
|---|---|---|
| AIDS (HTLV-1) | HIV-1 RT 476-484 | HLA-A2 |
| Influenza | G I L G F V F T L (SEQ ID NO: 16) | HLA-A2 |
| CMV disease | CMV | HLA-A2 |
| Burkitts Lymphoma | TAX | HLA-A2 |
| Hepatitis C | HCV | HLA-A2 |
| Hepatitis B | HBV pre-S protein 85-66 S T N R Q S G R Q (SEQ ID NO: 17) | HLA-A2 |
| HTLV-1 Leukemia | HTLV-1 tax 11-19 | HLA-A2 |
| Hepatitis | HBV surface antigen 185-194 | HLA-A2 |

Autoimmune MHC-Restricted Antigens:

The BMI Biomedical Informatics Heidelberg website provides examples of human MHC class I, autoimmune MHC-restricted peptides derived from autoimmune antigens.

Soluble MHC Class I Molecules:

Sequences encoding recombinant MHC class I and class II complexes which are soluble and which can be produced in large quantities are described in, for example, references 23, 24 and 41-53 and further in U.S. patent application Ser. No. 09/534,966 and PCT/IL01/00260 (published as WO 01/72768), all of which are incorporated herein by reference. Soluble MHC class I molecules are available or can be produced for any of the MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, following, for example the teachings of PCT/IL01/00260, as their sequences are known and can be found at the kabbat data base, the contents of the site is incorporated herein by reference. Such soluble MHC class I molecules can be loaded with suitable MHC-restricted antigens and used for vaccination of Non-human mammal having cells expressing the human major histocompatibility complex (MHC) class I as is further detailed hereinbelow.

Chemical Conjugates:

Many methods are known in the art to conjugate or fuse (couple) molecules of different types, including peptides or polypeptides. These methods can be used according to the present invention to couple a soluble human MHC class I effector domain with an antibody targeting domain and optionally with an MHC-restricted antigen.

Two isolated peptides can be conjugated or fused using any conjugation method known to one skilled in the art. One peptide can be conjugated to another using a 3-(2-pyridyldithio)propionic acid Nhydroxysuccinimide ester (also called N-succinimidyl 3-(2-pyridyldithio)propionate) ("SDPD") (Sigma, Cat. No. P-3415), a glutaraldehyde conjugation procedure or a carbodiimide conjugation procedure.

SPDP Conjugation:

Any SPDP conjugation method known to those skilled in the art can be used. For example, in one illustrative embodiment, a modification of the method of Cumber et al. (1985, Methods of Enzymology 112: 207-224) as described below, is used.

A peptide (1.7 mg/ml) is mixed with a 10-fold excess of SPDP (50 mM in ethanol) and the antibody is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS.

The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation:

Conjugation of a peptide with another peptide can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques, Academic Press, San Diego) described below, is used.

The peptides (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes)

Carbodiimide Conjugation:

Conjugation of a peptide with another peptide can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of one peptide (resulting in the formation of an ester bond), or an amino group of the one peptide (resulting in the formation of an amide bond) or a sulfhydryl group of the one peptide (resulting in the formation of a thioester bond).

Likewise, carbodiimide coupling can be used to form analogous covalent bonds between a carbon group of one peptide and an hydroxyl, amino or sulfhydryl group of the other peptide. See, generally, J. March, Advanced Organic Chemistry: Reaction's, Mechanism, and Structure, pp. 349-50 & 372-74 (3d ed.), 1985. By means of illustration, and not limitation, the peptide is conjugated to another via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Examples

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Peptides:

Peptides were synthesized by standard fluorenylmethoxycarbonyl chemistry and purified to >95% by reverse phase HPLC. The tumor associated HLA-A2-restricted peptides used are: G9-209-2M (IMDQVPFSV, SEQ ID NO:8) and G9-280-9V (YLEPGPVTV, SEQ ID NO:9), both derived from the melanoma differentiation antigen gp100 and are common immunodominant epitopes (32-34). These peptides are modified at the MHC anchor positions 2 (in G9-209-2M) and 9 (in G9-280-9V) to improve the binding affinity to HLA-A2 (27). The HTLV-1-derived peptide (LLFGYPVYV, SEQ ID NO:10) was used as control.

Cell Lines:

A431, ATAC4 (epidermoid carcinoma), HUT102W and CRII-2 (leukemia, ATL) cells were maintained in RPMI+ 10% FCS. ATAC4 cells are human epidermoid carcinoma A431 cells stably transfected with the IL-2 receptor α subunit (p55, Tac, CD25) (53). The transfected cells were maintained in growth medium containing 500 µg/ml G418 (Gibco-BRL).

Plasmid Constructions:

The scMHC molecule was constructed as previously described by linking human β2-microglobulin with the three extracellular domains of the HLA-A2 gene (24, 25, WO 01/72768). The VL(cys) and VH(cys) variable domain genes of the anti-Tac MAb were constructed previously to form the anti-Tac dsFv molecule in which the two variable domains are held together and stabilized by an interchain disulfide bond engineered at conserved framework residues (29, 30). To construct the scMHC-aTacVL molecule the C-terminus of the scMHC molecule was connected to the N-terminus of anti-Tac VL using a 15-residues long flexible linker (Gly$_4$-Ser)$_3$ (SEQ ID NO:3). PCR amplified cDNAs of both molecules were used in a two-step PCR overlap extension reaction in which the 3'-end of scMHC was connected to the 5'-end of the VL gene. In the first step two thirds of the linker sequence and cloning sites were introduced to either gene by using the oligonucleotides: scMHC-5: 5'GGAAGCGTTG-GCGCATATGATCC AGCGTACTCC-3' (SEQ ID NO:11) and scMHC-3: 5'-TCCTGAACCTCCGCCACCGGAC-CCTCCTCCGCCCTCCCATCTCAGGGT-3' (SEQ ID NO:12), which introduce an NdeI restriction site at the 5'-end of the scMHC gene and two third of the linker at the 3'-end. The anti-Tac VL gene was PCR amplified with the oligonucleotides: VL-Tac-5: 5'-TCCGGTGGCGGAGGTTCAG-GAGGCGGTGGATCGCAAATTGTTCTCACC-3' (SEQ ID NO:13) and VL-Tac-3: 5'-GCAGTAAGGAA TTCATTA-GAGCTCCAGCTTGGT-3' (SEQ ID NO:14) to introduce two third of the linker at the 5'-end of the VL gene and an EcoRI cloning site at the 3'-end. In a second assembly step the two PCR products were combined in a 1:1 ratio (50 ng each) to form a PCR overpap extension reaction using the primers scMHC-5 and VL-Tac-3 for the assembly of scMHC-aTacVL construct. The PCR product was subsequently subcloned into the pET-based expression vector pULI7 (49) using the NdeI and EcoRI restriction sites. The anti-Tac VH gene for making the anti-Tac dsFv fragment was subcloned into pULI7 as previously described (29).

Expression, Refolding and Purification of B2M-aTac (dsFv)-Peptide Complexes:

The components of the B2M-aTac(dsFv); the scMHC-aTacVL and aTac VH, were expressed in separate BL21 (λDE3) cells (Novagen, Madison, Wis.). Upon induction with IPTG, large amounts of insoluble recombinant protein accumulated in intracellular inclusion bodies. Inclusion bodies of each component were isolated and purified from the induced BL21 cells as previously described (29, 49). Briefly, cell disruption was performed with 0.2 mg/ml of lysozyme followed by the addition of 2.5% TRITON X-100 and 0.5 M NaCl. The inclusion bodies pellets were collected by centrifugation (13,000 RPM, 60 minutes at 4° C.) and washed 3 times with 50 mM Tris buffer, pH 7.4, containing 20 mM EDTA. Expression of each recombinant protein component in isolated and purified inclusion bodies was determined by analyzing a sample on SDS-PAGE as shown in FIG. 2B. The isolated and purified inclusion bodies were solubilized in 6 M Guanidine HCl, pH 7.4, followed by reduction with 65 mM DTE. Solubilized and reduced inclusion bodies of the scMHC-aTacVL and aTacVH, mixed in a 1:2 molar ratio, were refolded by a 1:100 dilution into a redox-shuffling buffer system containing 0.1 M Tris, 0.5 M Arginine, 0.09 mM Oxidized Glutathion, pH 10.0, in the presence of a 5-10 molar excess of the HLA-A2-restricted peptides. The final protein concentration in the refolding was 50 μg/ml. After refolding the protein was dialyzed against 100 mM Urea, 20 mM Tris, pH 7.4, followed by purification of soluble scMHC-aTac (dsFv)-peptide complexes by ion-exchange chromatography on Q Sepharose column (7.5 mm inner diameter×60 cm length, Pharmacia) applying a salt (NaCl) gradient (0-0.4 M). Peak fractions containing scMHC-aTac(dsFv) were then subjected to size-exclusion chromatography (TSK3000) for further purification and buffer exchange to PBS.

ELISA:

Immunoplates (Falcon) were coated with 10 μg/ml purified p55 antigen (overnight at 4° C.). Plates were blocked with PBS containing 2% skim milk and then incubated with various concentrations of B2M-aTac(dsFv)-peptide (90 minutes at room temperature). Binding was detected using the anti-HLA conformational dependent antibody W6/32 (60 minutes, room temperature, 10 μg/ml). The reaction was developed using anti-mouse IgG-peroxidase. Rabbit anti-Tac antibody was used as a positive control, followed by anti-rabbit peroxidase.

Flow Cytometry:

Cells were incubated with B2M-aTac(dsFv)-peptide complexes (60 minutes at 4° C. in 300 μl, 25 μg/ml) washed and incubated with the anti-HLA-A2 MAb BB7.2 (60 minutes at 4° C., μg/ml). Detection was with anti-mouse FITC. Human anti Tac (10 μg/ml) was used as positive control to determine the expression of the p55 antigen followed by incubation with anti human FITC labeled antibody. Cells were subsequently washed and analyzed by Beckman FACScaliber flow cytometer.

CTL Clones and Stimulation:

CTL clones specific for the melanoma gp100-derived peptides were provided by Drs. Steven Rosenberg and Mark Dudley, Surgery Branch, National Cancer Institute, NIH. These CTL clones were generated by cloning from bulk cultures of PBMCs from patients receiving peptide immunizations (26). CTL clones were expanded by incubation with irradiated melanoma FM3D cells (as a source of antigen) and the EBV-transformed JY cells (B-lymphoblasts as antigen-presenting cells). The stimulation mixture contained also the OKT3 antibody (30 ng/ml) and 50 IU/ml of IL-2 and IL-4.

Cytotoxicity Assays:

Target cells were cultured in 96 well plate (2–5×10$^3$ cells per well) in RMPI+10 FCS. Cells were washed and incubated with methionine and serum-free medium for 4 hours followed by incubation (over night) with 15 μCi/ml of $^{35}$S-methionine (NEN). After 3 hours incubation with B2M-aTac(dsFv)-peptide complexes (at 37° C., 10-20 μg/ml), effector CTL cells were added at target:effctor ratio as indicated and incubated for 8-12 hours at 37° C. Following incubation, $^{35}$S-methionine release from target cells was measured in a 50 μl sample of the culture supernatant. All assays were performed in triplicates. The percent specific lysis was calculated as follows: [(experimental release−spontaneous release)/(maximum release−spontaneous release)]×100. Spontaneous release was measured as $^{35}$S-methionine released from target cells in the absence of effector cells, and maximum release was measured as $^{35}$S-methionine released from target cells lysed by 0.1 M NaOH.

Experimental Results

Design of B2M-antiTac(dsFv):

Recently a construct encoding a soluble single-chain MHC (scMHC) was generated in which the human β-2 microglobulin gene is linked to the three extracellular domains (α1, α2 and α3) of the HLA-A2 heavy chain gene (aa 1-275) through a 15-amino acid-long flexible linker (24, 25 and WO 01/72768, which is incorporated herein by reference). These scMHC molecules were expressed in E. coli as intracellular inclusion bodies and upon in vitro refolding in the presence of HLA-A2-restricted tumor associated or viral peptides they form correctly folded and functional scMHC-peptide complexes and tetramers (24, 25, WO 01/72768). These scMHC-peptide complexes have been characterized in detail for their biochemical and biophysical characteristics as well as for their biological activity and found to be functional (24, 25, WO 01/72768). Most importantly, they were able to bind and stain tumor-specific CTL lines and clones. Shown in FIGS. 1A-H are the construction and reactivity of these scMHC-peptide complexes, in the form of scMHC tetramers, with CTLs specific for the melanoma differentiation antigen gp100 epitopes G9-209M and G9-280V (26). These peptides are modified at the MHC anchor positions 2 (in G9-209M) and 9 (in G9-280V) to improve the binding affinity to HLA-A2 (27). The CD8$^+$ CTL clones (FIGS. 1A and 1D) R6C12 and R1E2 were stained intensively (80-95%) and specifically with the G9-209M and G9-280V-containing scMHC tetramers, respectively (FIGS. 1B and 1E). As specificity control, the G9-209M-specific R6C12 and G9-280V-specific R1E2 CTLs were not stained by G9-280V and G9-209M scHLA-A2 tetramers, respectively (FIGS. 1C and 1F). These CTLs also reacted with a similar intensity with the wild-type unmodified epitopes G9-209 and G9-280 (data not shown).

To generate the B2M-aTac(dsFv) molecule which targets the scMHC molecule to cells through the use of an antibody Fv fragment, at the C-terminus of the HLA-A2 gene, was fused the light chain variable domain (VL) gene of the humanized anti CD25 (also known as Tac, p55, IL-2R α subunit) monoclonal antibody anti-Tac (28) (FIG. 2A). The heavy chain variable domain (VH) is encoded by another plasmid to form a disulfide-stabilized Fv antibody fragment (dsFv) in which the VH and VL domains are held together and stabilized by an interchain disulfide bond engineered between structurally conserved framework residues of the Fv (FIGS. 2A, 2E and 2F) (29,30). The positions at which the cysteine residues are placed were identified by computer-based molecular modeling; as they are located in the framework of each VH and VL, this location can be used as a general method to stabilize all Fvs without the need for further structural information. Many dsFvs have been constructed in the past few years, which have been characterized in detail and found to be extremely stable and with binding affinity as good as other forms of recombinant antibodies and in many cases even improved (30, 31).

Construction, Expression and Purification of B2M-antiTac (dsFv):

To generate the B2M-aTac(dsFv) molecule, two T7 promoter-based expression plasmids were constructed (see also Materials and Experimental Methods section hereinabove); the scMHC molecule fused to anti-Tac VL domain (B2M-aTacVL) is encoded by one plasmid and the anti-Tac VH domain is encoded by the second. In both plasmids the VL and VH domains contain a cysteine which was engineered instead of a conserved framework residue to form a dsFv fragment (30). The expression plasmid for the B2M-aTacVL was generated by an overlap extension PCR reaction in which the HLA-A2 and VL genes were linked by a flexible 15-amino acid—long linker of [(gly$_4$-ser)$_3$, (SEQ ID NO:3)] which is identical to the linker used to connect the J32-microglobulin and HLA-A2 genes in the scMHC construct (24, 25, WO 01/72768). The construction of the expression plasmid for the anti-Tac VH domain was described previously (29). The two plasmids were expressed separately in E. coli BL21 cells. Upon induction with IPTG, large amounts of recombinant protein accumulated in intracellular inclusion bodies. SDS-PAGE analysis of isolated and purified inclusion bodies demonstrated that recombinant proteins with the correct size constituted 80-90% of total inclusion bodies protein (FIG. 2B). The inclusion bodies of each component were isolated separately, solubilized, reduced, and refolded in a renaturation buffer which contained redox-shuffling and aggregation-preventing additives, in the presence of HLA-A2-restricted peptides derived from the melanoma differentiation antigen gp100 T cell epitopes G9-209M and G9-280V (32-34, 27). The solubilized and reduced components, B2M-aTacVL and anti-TacVH were mixed in a 1:2 molar ratio in the presence of a 100-fold molar excess of the HLA-A2 restricted peptide. scMHC-peptide complexes and antibody Fv-fusion proteins generated previously using this refolding protocol were found to be folded correctly and functional (24, 25, 30). B2M-aTac(dsFv)/peptide molecules (complexes) were purified from the refolding solution by ion-exchange chromatography using Q-Sepharose columns. As shown in FIG. 2C, non-reducing SDS-PAGE analysis of peak fractions eluted from the MonoQ column revealed the presence of monomeric B2M-aTac(dsFv) molecules with the correct molecular weight of about 67 kDa. These factions contained also B2M-aTacVL single-domain molecules that were not paired with the VH. These single-domain B2M molecules are difficult to separate from the B2M-dsFv molecules because, as also previously shown with other dsFv-fusion proteins, VL-fusions folding is very efficient and the product is quite soluble. However, the contamination with the single-domain B2M molecules did not interfere with subsequent analyses of the soluble B2M-aTac(dsFv) molecule. To confirm the correct formation of the dsFv fragment, a reducing SDS-PAGE analysis was performed in which the B2M-dsFv molecule was separated to its components. Shown (FIG. 2D) is the molecular form of the B2M-aTac(dsFv) after reduction containing the B2M-aTacVL and the VH domains. In any case, other size separation techniques can be used to purify the B2M-aTac(dsFv) molecule to homogeneity.

The ability of the B2M-aTac(dsFv) to bind its target antigen, the α subunit of the IL-2 receptor (p55), was tested first by ELISA using purified p55. To monitor binding of the purified B2M-aTac(dsFv) to p55-coated wells the monoclonal antibody w6/32 was used, which recognizes HLA molecules only when folded correctly and contain peptide. As shown in FIG. 2E, B2M-aTac(dsFv) binds in a dose dependent manner to p55 which indicates that the two functional domains of the molecule, the scMHC effector domain and the antibody dsFv targeting domain, are folded correctly, indicated by the ability of the dsFv moiety to bind the target antigen and the recognition of the scMHC by the conformational-specific anti-HLA antibody.

Binding of B2M-aTac(dsFv) to Target Cells:

To test the ability of the B2M-aTac(dsFv) molecule to coat and target HLA-A2-peptide complexes on tumor cells, its binding to HLA-A2 negative tumor cells was tested by flow cytometry. First, A431 human epidermoid carcinoma cells were used, that were stably transfected with the p55 gene (ATAC4 cells) (35) and the staining of transfected versus non-transfected parental cells was tested. The binding of B2M-aTac(dsFv) to the cells was monitored using an anti-HLA-A2 MAb BB7.2 and FITC-labeled secondary antibody. Expression of the p55 target antigen was detected by the whole anti-Tac monoclonal antibody from which the dsFv fragment was derived. As shown in FIG. 3A, A431 cells do not express p55, however, the p55-transfected ATAC4 cells express high levels of the antigen (FIG. 3B). Neither cell line was HLA-A2 positive (FIGS. 3C and 3D). When testing the binding of B2M-aTac(dsFv) to these cells, FIGS. 3C and 3D show that ATAC4 cells gave a positive anti-HLA-A2 staining only when preincubated with B2M-aTac(dsFv) (FIG. 3D), but A431 cells were negative when preincubated with B2M-aTac(dsFv).

Next, the binding was tested of B2M-aTac(dsFv) to leukemic cells which, as shown in FIG. 3E, express the p55 antigen but lack HLA-A2 expression (FIG. 3F). As shown in FIG. 2F, the ATL leukemic HUT102W cells expressing p55, gave a positive anti-HLA-A2 staining when preincubated with the B2M-aTac(dsFv). Similar results were observed when leukemia (ATL) p55-positive, HLA-A2-negative CRII-2 cells were preincubated with the B2M-aTac(dsFv) molecule (data not shown). These results demonstrate that B2M-aTac(dsFv) can bind to its antigen as displayed in the native form on the surface of cells. Most importantly, B2M-aTac(dsFv) could be used to coat HLA-A2 negative cells in a manner that was entirely dependent upon the specificity of the tumor targeting antibody fragment rendering them HLA-A2 positive cells.

Induction of B2M-aTac(dsFv)-Mediated Susceptibility to CTL Lysis:

To test the ability of B2M-aTac(dsFv) to potentiate the susceptibility of HLA-A2 negative cells to CTL-mediated killing radiolabeled target cells were first incubated with B2M-aTac(dsFv) and then tested in a $^{35}$S-methionine-release assay in the presence of HLA-A2-restricted melanoma gp100-peptide-specific CTL. As shown in FIG. 4A, B2M-aTac(dsFv) induced an efficient CTL-mediated lysis of p55-positive HLA-A2 negative ATAC4 cells while the same B2M-aTac(dsFv) molecule did not have any effect and induced no lysis of A431 cells that do not express the antigen. A431 and ATAC4 cells alone did not exhibit any CTL-mediated lysis (FIG. 4A). Incubation of ATAC4 cells with scMHC alone, not fused to the dsFv targeting moiety, or with the anti-Tac antibody did not result in any detectable potentiation of CTL-mediated lysis (data not shown). The capacity of G9-209M-peptide-specific CTLs to kill B2M-aTac(dsFv)-preincubated ATAC4 cells (but not A431 cells) was as good, and in many experiments better, as the efficiency of these CTLs to lyse melanoma FM3D cells which express high levels of HLA-A2 and the gp100 melanoma differentiation antigen (36) (FIG. 4B). To demonstrate the specificity of B2M-aTac(dsFv)-mediated CTL killing for the HLA-A2-restricted antigenic peptide used in the refolding of the B2M-aTac(dsFv) molecule, two CTL clones were used, specific for the gp100 major T cell epitopes G9-209M and G9-280V. As shown in FIG. 4C, p55-positive, HLA-A2-negative ATAC4 cells were lysed by the G9-209M-peptide-specific CTL clone R6C12 only when preincubated with B2M-aTac(dsFv) refolded with the G9-209M peptide but not with the G9-280V epitope derived from the same melanoma differentiation antigen nor with B2M-aTac(dsFv) refolded around the HTLV-1 HLA-A2-restricted T cell epitope TAX. Similarly, ATAC4 cells were killed by the G9-280V-specific CTL clone R1E2 only when preincubated with B2M-aTac(dsFv) refolded with the G9-280V epitope but not with the G9-209M or TAX peptides (FIG. 4D). Next, B2M-aTac(dsFv)-mediated CTL lysis of p55 expressing, HLA-A2 negative leukemic cells HUT102W and CRII-2 was tested. As shown in FIG. 4E, HUT102W and CRII-2 were not susceptible to lysis by the HLA-A2-restricted CTL clones R6C12 and R1E2, specific for the G9-209M and G9-280V gp100 peptides, respectively. However, when these p55-positive, HLA-A2-negative target cells were preincubated with the B2M-aTac(dsFv) molecule a significant potentiation for CTL-mediated lysis was observed which was specific for the gp100 peptide present in the B2M-aTac(dsFv) complex (FIG. 4E). B2M-aTac(dsFv) coated-HUT102W cells were efficiently killed by the G9-209M and G9-280V peptide-specific R6C12 and R1E2 CTL clones, respectively and CRII-2 cells were lysed by the R1E2 CTL clone. Control non-melanoma HLA-A2 positive and negative target cells that do not express p55 did not exhibit any detectable susceptibility to lysis by the melanoma-specific CTL clones weather coated or not with the B2M-aTac(dsFv) molecule (data not shown). These results clearly demonstrate, in vitro, the concept that the B2M-aTac(dsFv) construct can be used efficiently for antibody-guided, tumor antigen-specific targeting of MHC-peptide complexes on tumor cells to render them susceptible to lysis by relevant CTLs and thus, potentiate anti-tumor immune responses.

In Vivo Activity of B2M-aTac(dsFv):

To initially evaluate the in vivo activity of B2M-aTac(dsFv) in a human tumor model, a win-type assay in which ATAC4 cells were mixed with R6C12 CTLs specific for the G9-209M gp100-derived peptide was performed in the presence or absence of the B2M-aTac(dsFv) molecule. The mixture was injected subcotaneously to nude mice and formation of human xenografts in the animals was followed. As shown in FIG. 5, ATAC4 cells generated xenografts in nude mice 10-12 days after subcutaneous injection.

A mixture of ATAC4 and R6C12 CTLs did not exhibit any significant effect on tumor growth. However, when IL-2 receptor expressing ATAC4 cells were mixed with B2M-aTac(dsFv) and R6C12 CTLs complete inhibition of tumor growth was observed indicating the efficient B2M-aTac(dsFv)-induced, CTL-mediated, killing of ATAC4 target cells in vivo. In vitro results (FIGS. 4A-E) confirmed that the amount of B2M-aTac(dsFv) and the effector to target ratio used for the in vivo assay resulted in maximal lysis of ATAC4 target cells (95-100% killing). Parental IL-2 receptor negative A431 cells mixed with R6C12 CTLs in the presence or absence of B2M-aTac(dsFv) generated tumors efficiently, whereby no effect on tumor growth was observed (not shown).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Gilboa, E. (1999) How tumors escape immune destruction and what we can do about it. *Cancer Immunol Immunother.* 48, 343-5
2. Seliger B, Maeurer M J, Ferrone S (2000) Antigen-processing machinery breakdown and tumor growth. *Immunol Today.* 21, 455-64.
3. Gamido F, Algarra I. (2001) MHC antigens and tumor escape from immune surveillance. Adv Cancer Res.; 83:117-58.
4. Ferrone S, Finerty J F, Jaffee E M, Nabel G J. (2000) How much longer will tumour cells fool the immune system? *Immunol Today.* 21, 70-2.

5. Marincola F M, Jaffee E M, Hicklin D J, Ferrone S. (2000) Escape of human solid tumors from T-cell recognition: molecular mechanisms and functional significance. *Adv Immunol.* 74, 181-273.
6. Rosenberg, S. A. (2001) Progress in human tumour immunology and immunotherapy. *Nature* 411, 380-4
7. Lee, P. P. et al. (1999) Characterization of circulating T cells specific for tumor-associated antigens in melanoma patients. *Nat. Med.* 5, 677-685.
8. Mocellin S, Wang E, Marincola F M. (2001) Cytokines and Immune Response in the Tumor Microenvironment. *J. Immunother.* 24, 392-407.
9. Offringa, R., van der Burg, S. H., Ossendorp, F. Toes, R. E., & Melief, C. J. Design and evaluation of antigen-specific vaccination strategies against cancer. (2000)*Curr Opin Immunol* 12, 576-82.
10. Esche, C., Shurin, M. R., Lotze, M. T., (1999) The use of dendritic cells for cancer vaccination. *Curr Opin Mol Ther* 1, 72-81
11. Wang E, Phan G Q, Marincola F M. (2001) T-cell-directed cancer vaccines: the melanoma model. *Expert Opin Biol Ther.* 1, 277-90.
12. Boon, T., & van der Bruggen, P. (1996) Human tumor antigens recognized by T lymphocytes. *J Exp Med* 183, 725-9.
13. Renkvist, N., Castelli, C., Robbins, P F, & Parmiani, G. (2001) A listing of human tumor antigens recognized by T cells. *Cancer Immunol Immunother* 50, 3-15
14. Ferrone S, Marincola F M. (1995) Loss of HLA class I antigens by melanoma cells: molecular mechanisms, functional significance and clinical relevance. *Immunol Today.* 16, 487-94.
15. Hicklin D J, Marincola F M, Ferrone S. (1999) HLA class I antigen downregulation in human cancers: T-cell immunotherapy revives an old story. *Mol Med Today* 5, 178-86.
16. Mendez R, et al. (2001) Analysis of HLA class I expression in different metastases from two melanoma patients undergoing peptide immunotherapy. *Tissue Antigens.* 57, 508-19.
17. Real L M, (2001) et al Multiple mechanisms of immune evasion can coexist in melanoma tumor cell lines derived from the same patient. *Cancer Immunol Immunother.* 49, 621-8.
18. Restifo N P, Marincola F M, Kawakami Y, Taubenberger J, Yannelli J R, Rosenberg S A. (1996) Loss of functional beta 2-microglobulin in metastatic melanomas from five patients receiving immunotherapy. *J Natl Cancer Inst.* 88, 100-8.
19. Seliger B, Maeurer M J, Ferrone S. (1997) TAP off—tumors on. *Immunol Today* 18, 292-9.
20. Vitale M, et al (1998) HLA class I antigen and transporter associated with antigen processing (TAP1 and TAP2) down-regulation in high-grade primary breast carcinoma lesions. *Cancer Res.* 58, 737-42.
21. Johnsen A, France J, Sy M S, Harding C V. (1998) Down-regulation of the transporter for antigen presentation, proteasome subunits, and class I major histocompatibility complex in tumor cell lines. *Cancer Res.* 58, 3660-7.
22. Hudson P J, Souriau C. (2001) Recombinant antibodies for cancer diagnosis and therapy. Expert *Opin Biol Ther.* 1, 845-55.
23. Cheng J D, Rieger P T, von Mehren M, Adams G P, Weiner L M. (2000) Recent advances in immunotherapy and monoclonal antibody treatment of cancer. *Semin Oncol Nurs.* 16, 2-12.
24. Denkberg, G., Cohen, C. J., Segal, D., Kirkin, A. F. & Reiter, Y. (2000) Recombinant human single-chain MHC-peptide complexes made from *E. coli* by in vitro refolding: functional single-chain MHC-peptide complexes and tetramers with tumor associated antigens. *Eur. J. Immunol.* 30, 3522-3532.
25. Denkberg, G., Cohen, C. J., & Reiter, Y. (2001) Critical role for cd8 in binding of mhc tetramers to tcr: cd8 antibodies block specific binding of human tumor-specific mhc-peptide tetramers to TCR. *J Immunol* 167, 270-6
26. Dudley, M. E., Ngo, L. T., Westwood, J., Wunderlich, J. R. & Rosenberg, S. A. (2000) T-cell clones from melanoma patients immunized against an anchor-modified gp100 peptide display discordant effector phenotypes. *Cancer J.* 6, 69-77
27. Parkhurst M R, et al (1996) Improved induction of melanoma-reactive CTL with peptides from the melanoma antigen gp100 modified at HLA-A*0201-binding residues. *J. Immunol.* 157, 2539-48.
28. Uchiyama T, Broder S, Waldmann T A. (1981) A monoclonal antibody (anti-Tac) reactive with activated and functionally mature human T cells. I. Production of anti-Tac monoclonal antibody and distribution of Tac (+) cells. *J Immunol* 126, 1393-7.
29. Reiter Y, Kreitman R J, Brinkmann U, Pastan I. (1994) Cytotoxic and antitumor activity of a recombinant immunotoxin composed of disulfide-stabilized anti-Tac Fv fragment and truncated *Pseudomonas* exotoxin. *Int J. Cancer.* 58, 142-9.
30. Reiter Y, Brinkmann U, Lee B, Pastan I. (1996) Engineering antibody Fv fragments for cancer detection and therapy: disulfide-stabilized Fv fragments. *Nat. Biotechnol.* 14, 1239-45.
31. Reiter Y, Brinkmann U, Jung S H, Lee B, Kasprzyk P G, King C R, Pastan I. (1994) Improved binding and antitumor activity of a recombinant anti-erbB2 immunotoxin by disulfide stabilization of the Fv fragment. *J Biol. Chem.* 269, 18327-31.
32. Bakker, A. B. et al. (1994) Melanocyte lineage-specific antigen gp100 is recognized by melanoma-derived tumor-infiltrating lymphocytes. *J. Exp. Med.* 179, 1005-1009.
33. Kawakami, Y. et al. (1995) Recognition of multiple epitopes in the human melanoma antigen gp100 by tumor-infiltrating T lymphocytes associated with in vivo tumor regression. *J. Immunol.* 154, 3961-3968
34. Cox, A. L. et al. (1994) Identification of a peptide recognized by five melanoma-specific human cytotoxic T cell lines. *Science* 264, 716-719
35. Kreitman R J, Bailon P, Chaudhary V K, FitzGerald D J, Pastan I. (1994) Recombinant immunotoxins containing anti-Tac(Fv) and derivatives of *Pseudomonas* exotoxin produce complete regression in mice of an interleukin-2 receptor-expressing human carcinoma. *Blood* 83, 426-34.
36. Kirkin, A. F. et al. (1995) Generation of human-melanoma-specific T lymphocyte clones defining novel cytolytic targets with panels of newly established melanoma cell lines. *Cancer Immunol. Immunother.* 41, 71-81
37. Pastan, I. (1997) Targeted therapy of cancer with recombinant immunotoxins. *Biochim Biophys Acta.* 1333, $C_{1-6}$
38. Lode, H. N., & Reisfeld, R. A. (2000) Targeted cytokines for cancer immunotherapy. *Immunol Res.* 21, 279-88
39. Withoff, S., Helfrich, W., de Leij, L F., Molema, G. (2001) Bi-specific antibody therapy for the treatment of cancer. *Curr Opin Mol. Ther.* 3:53-62
40. Jain R K. (1999) Transport of molecules, particles, and cells in solid tumors. *Annu Rev Biomed Eng.* 1, 241-63.

41. Robert B, Guillaume P, Luescher I, Romero P, Mach J P. (2000) Antibody-conjugated MHC class I tetramers can target tumor cells for specific lysis by T lymphocytes. *Eur J Immunol.* 30, 3165-70.
42. Lanzavecchia, A., G. Lezzi, and A. Viola. (1999) From TCR engagement to T cell activation: a kinetic view of T cell behaviour. *Cell* 96, 1-4
43. Bromley, S K, et al (2001) The immunological synapse. *Ann Rev. Immunol.* 19, 375-396.
44. Wang, B., R. Maile, R. Greenwood, E. J. Collins, and J. A. Frelinger. (2000) Naive CD8+ T cells do not require costimulation for proliferation and differentiation into cytotoxic effector cells. *J. Immunol.* 164, 1216-1222.
45. Tussey L, Speller S, Gallimore A, Vessey R. (2000) Functionally distinct CD8+ memory T cell subsets in persistent EBV infection are differentiated by migratory receptor expression. Eur J. Immunol. 30, 1823-9.
46. Lechner F, Cuero A L, Kantzanou M, Klenerman P. (2001) Studies of human antiviral CD8+ lymphocytes using class I peptide tetramers. *Rev Med. Virol.* 11, 11-22.
47. Mottez, E., P. Langlade-Demoyen, H. Gournier, F. Maranon, J. Maryanski, P. Kourilsky, and J. P. Abastado. (1995) Cells expressing a major histocompatibility complex class I molecule with a single covalently bound peptide are highly immunogenic. J. Exp. Med. 181, 493-7
48. White, J., Crawford, F., Fremont, D., Marrack, P., and Kappler, J. (1999) Soluble class I MHC with −2 microglobulin covalently linked peptides: specific binding to a T-cell hybridoma. *J. Immunol.* 162, 2671-8
49. Brinkmann U, Pai L H, FitzGerald D J, Willingham M, Pastan I. (1991) B3(Fv)-PE38 KDEL, a single-chain immunotoxin that causes complete regression of a human carcinoma in mice. *Proc Natl Acad Sci USA.* 88, 8616-20.
50. Kreitman R J. Chimeric fusion proteins—*Pseudomonas* exotoxin-based (2001). *Curr Opin Investig Drugs.*, 2, 1282-93.
51. Pastan I I, Kreitman R J. (1998) Immunotoxins for targeted cancer therapy. *Adv Drug Deliv Rev.* 31, 53-88.
52. Frankel A E, Kreitman R J, Sausville E A. (2000) Targeted toxins. *Clin Cancer Res.* 6, 326-34.
53. Kreitman R J, Bailon P, Chaudhary V K, FitzGerald D J, Pastan I. (1994) Recombinant immunotoxins containing anti-Tac(Fv) and derivatives of *Pseudomonas* exotoxin produce complete regression in mice of an interleukin-2 receptor-expressing human carcinoma. *Blood* 83, 426-34.

What is claimed is:

1. A method of selectively killing a tumor cell in a patient, the cell presenting an antigen, the method comprising administering to the patient a molecule which comprises consecutive amino acids present in the following consecutive segments, beginning at the amino terminus of the molecule: (i) a human MHC-restricted peptide capable of eliciting a memory response when present in the molecule, (ii) a first peptide linker, (iii) a human β-2 microglobulin, (iv) a second peptide linker, (v) a human MHC class I molecule, and (vi) an antibody targeting domain which comprises an association of a heavy chain variable region and a light chain variable region, wherein said antibody is specific to said antigen, wherein the consecutive amino acids which correspond to segments (v) and (vi) are linked to each other directly by a peptide bond or by a third peptide linker and wherein the carboxyl terminus of each of segments (i) through (v) is covalently linked to the amino terminus of segments (ii) through (vi), respectively, whereby said molecule initiates a CTL mediated immune response against said cell, thereby selectively killing the tumor cell.

2. The method of claim 1, wherein the human MHC-restricted peptide of segment (i) is from a viral protein.

3. The method of claim 2, wherein the viral protein is CMV.

4. The method of claim 2, wherein said viral protein is from an influenza.

5. The method of claim 1, wherein segment (v) is linked either directly by a peptide bond or by a third peptide linker to the light chain variable region of segment (vi).

6. The method of claim 1, wherein the heavy chain variable region and light chain variable region are linked to each other by intermolecular disulfide bonds.

7. The method of claim 1, wherein the heavy chain variable region and light chain variable region are linked to each other by a fourth peptide linker.

8. The method of claim 1, wherein said antigen is EGFR.

9. The method of claim 1, wherein said antigen comprises CD25.

10. The method of claim 8, wherein said tumor cell is a lung cancer cell, a brain tumor cell or a breast cancer cell.

* * * * *